United States Patent
Gao et al.

(10) Patent No.: US 8,252,293 B2
(45) Date of Patent: Aug. 28, 2012

(54) **BINDING DOMAIN OF *PLASMODIUM* RETICULOCYTE BINDING PROTEINS**

(75) Inventors: Xiaohong Gao, Singapore (SG); Peter Preiser, Singapore (SG)

(73) Assignee: Nanyang Technological University, Singapore (SG)

( * ) Notice: Subject to any disclaimer, the term of this patent is extended or adjusted under 35 U.S.C. 154(b) by 445 days.

(21) Appl. No.: 12/441,092

(22) PCT Filed: Sep. 13, 2007

(86) PCT No.: PCT/SG2007/000312
§ 371 (c)(1),
(2), (4) Date: Mar. 12, 2009

(87) PCT Pub. No.: WO2008/033106
PCT Pub. Date: Mar. 20, 2008

(65) Prior Publication Data
US 2010/0297131 A1 Nov. 25, 2010

Related U.S. Application Data

(60) Provisional application No. 60/825,655, filed on Sep. 14, 2006.

(51) Int. Cl.
*A61K 39/015* (2006.01)
(52) U.S. Cl. .................. 424/268.1; 424/185.1; 530/350
(58) Field of Classification Search .......................... None
See application file for complete search history.

(56) References Cited

U.S. PATENT DOCUMENTS

2002/0127241 A1* 9/2002 Narum et al. .............. 424/191.1

OTHER PUBLICATIONS

Rayner et al. Am. J. Trop. Med. Hyg., 72(6), 2005, pp. 666-674.*
Skolnick et al., Trends in Biotechnology, 2000, 18(1):34-39.*
Whisstock et al., Quarterly Reviews of Biophysics, 2003, 36:307-340.*
Galinski et al., Cell, 1992, 69:1213-26.*
Rayner et al., J Exp. Med., 2001, 194:1571-1581.*
Valbuena et al., Peptides. Jul. 2003:24(7)1007-14.*
Ocampo et al., Parasitol Int. Mar. 2004;53(1):77-88.*
Rayner, J.C., et al. "Dramatic difference in diversity between *Plasmodium falciparum* and *Plasmodium vivax* reticulocyte binding-like genes." Am J Trop Med Hyg. Jun. 2005;72(6):666-74.
Ocampo, M., et al. "Identification of *Plasmodium falciparum* reticulocyte binding protein RBP-2 homologue a and b (PfRBP-2-Ha and -Hb) sequences that specifically bind to erythrocytes." Parasitol Int. Mar. 2004;53(1):77-88.
GenBank: AF411929.2. "*Plasmodium falciparum* strain FVO normocyte-binding protein 1 (NBP1) gene, complete cds." Entered Dec. 5, 2001.

* cited by examiner

*Primary Examiner* — Michael Szperka
(74) *Attorney, Agent, or Firm* — Dann, Dorfman, Herrell & Skillman; Kathleen D. Rigaut

(57) ABSTRACT

The present invention provides isolated polynucleotides, polypeptides, antibodies and/or vaccines for the prevention and/or treatment of malaria caused by *Plasmodium falciparum* and/or *Plasmodium vivax*. In particular, the polypeptide fragments are derived from the binding domain of the reticulocyte binding proteins of *Plasmodium falciparum* and/or *Plasmodium vivax*. The present invention also provides recombinant vaccines and their use in the prevention and/or treatment of malaria.

6 Claims, 7 Drawing Sheets

*Plasmodium falciparum* binding regions

>PFRH1-RII-3 (500-833aa)(1498-2499bp)(8301bp)
LQIVQQKLLEIKQKKNDITHKVQLINHIYKNIHDEILNKKNNEITKIIINNNIKDHKKDLQDLLLF
IQQIKQYNILTDHKITQCNNYYKEIIKMKEDINHIHIYIQPILNNLHTLKQVQNNKIKYEBHIKQ
ILQKTYDKKESLKKIILLKDEAQLDITLLDDLIQKQTKKQTQTQTQTQKQTLIQNNETIQLISGQ
EDKHESNPFNHIQTYIQQKDTQNKNIQNLLKSLYNGNINTFIDTISKYILKQKDIELTQHVYTDE
KINDYLEEIKNEQNKIDKTIDDIKTQETLKQITHIVNNIKTIKKDLLKEFIQHLIKYMNERYQNM
QQGYNNLTN

>PFRH2A (2251-2635aa) (6750-7905bp)(9393bp)
LEETQDKLLELYENFKKEKNIINNNYKIVHFNKLKEIENSLETYNSISTNFNKINETQNIDILKN
EFNNIKTKINDKVKELVHVDSTLTLESIQTFNNLYGDLMSNIQDVYKYEDINNVELKKVKLYIEN
ITNLLGRINTFIKELDKYQDENNGIDKYIEINKENNSYIIKLKEKANNLKENFSKLLQNIKRNET
ELYNINNIKDDIMNTGKSVNNIKQKPSSNLPLKEKLFQMEEMLLNINNNIMNETKRISNTAAYTNI
TLQDIENNKNKENNNMNIETIDKLIDHIKIHNEKIQABILIIDDAKRKVKEITDNINKAFNEITE
NYNNENN

>PFRH2B (151-485aa)(453-1455bp)(3348bp)
LEETQDKLLELYENFKKEKNIINNNYKIVHFNKLKEIENSLETYNSISTNFNKINETQNIDILKN
EFNNIKTKINDKVKELVHVDSTLTLESIQTFNNLYGDLMSNIQDVYKYEDINNVELKKVKLYIEN
ITNLLGRINTFIKELDKYQDENNGIDKYIEINKENNSYIIKLKEKANNLKENFSKLLQNIKRNET
ELYNINNIKDDIMNTGKSVNNIKQKFSSMLPLKEKLFQMEEMLLNINNNIMNETKRISNTDAYTNI
TLQDIENNKNKENNNMNIETIDKLIDHIKIHNEKIQAEILIIDDAKRKVKEITDNINKAFNEITE
NYNNENN

>PFRH4 (451-792aa)(1353-2374bp)(5094bp)
LNKFMQNETFKKNIDDKIKEMNNIYDNIYIIILKQKFLNKLNEIIQNHKNKQETKLNTTTIQELLQ
LLKDIKEIQTKQIDTKINTFNMYYNDIQQIKIKINQNEKEIKKVLPQLYIPKNEQEYIQIYKNEL
KDRIKETQTKINLPKQILELKEKEHYITNKHTYLNFTHKTIQQILQQQYKNNTQEKNTLAQFLYN
ADIKKYIDELIPITQQIQTKMYTTNNIEHIKQILINYIQECKPIQNISEHTIYTLYQEIKTNLEN
IEQKIMQNIQQTTNRLKINIKKIFDQINQKVDDLTKNINQMND

>PFRH3 (601-1135aa)(1803-3405bp)(8379bp)
INEIKSKMDNINEKLKHITDFIDKNVNYIYENHSTQDINIMLNNTISEYNKLEFINSDIFDNISK
KLKKELQDLVTLKESLMKMNHNVLKMDPLKSLNQVLEKYEELKKNINEYSKEENKLYDFKKQMES
RLNAFITNLNNNDETLVDGKNIYDQFVEYKEQLLIKKRIIINNNEIVIINDEVKKIKDELKSYNIL
SYKLENDTSHDVVNSVENTPSSDVATAVSNSSSILSTYNSTELNKLRNFFSEKDDELNVESKVKQ
DENIFIEKNKIFDDIIKDIELYNKKTNAIKNLNNAIMGSMNNLSLIDSVMKNKGDIINRLSQRSY
LIQTDNFIDIYEKIFLKDNLNKGLEEIENRLSNTYMNELKIEAEKQNEKYKKLKENINTYDDTFL
EKLIGDNYEWEVLKIELNGLNVNYNILQANIDTLIIKPYIDHIDHIISLIESLKHNIENKIKKVI
PNLERLKDFIQTKFNTNDIKLDHNNLIT

*Plasmodium vivax* binding regions

>PVRBP-1 (551-856aa)(1650-2568bp)(8622bp)
INDLQDLIDQMKEYKDEIVNNSEFISNRYKNIYENLKETYETELNDIGKLENDTSKVNFYLMQIR
KINTEKTKIDESLQTVEKFYKEILDSKEKIYELKIEFRKSVTEINRLQDGESARDLHEEQIKEIL
DKMAKKVHYLKELLSLKGKSSVYFTEMNELLNTASYDNMEGFSAKKEKADNDINALYNSVYREDI
NALIEEVEKFVTENKESTLEMLKDEBMESKLQDAKETFAKLNFVSDDKLTDVYTKMSAEVTNAEG
IKKEIAQKQFENVHKKMKEFSDAFSTKFEALQNSMQQYNQEGD

>PVRBP-2 (401-829aa)(1203-2487bp)(8604bp)
LQKVESDIYRVELKTLFYVAAKHYADFKFSLEHLKMFENLSKSKEKMLYSTFEKLEGDLLNKINT
LMGSEQSTSDLTSIIADSEKIIKSAESLINSSSEEIAKYALDSNEKINEIKKNYDQNILKVREFI
NKSNGLITSVKGTSQLSESDKQQIETKIEEIKKKKKDILERGKEFINIMNEIKKKKKSNSSNSST
NSKEFTDKLKELETEFEGLNKTVKGYLQEIEDIKVKENEDRSLKNQIEQHLKYTSDNRDNVKTLI
SKNDEIQKYIEKTEKLINDAPSGKDKFTTEKTNLQNKVKKIIDEFHKEDLQLLLNSLSKFYEEHQ
KLYNEASTIEKIKDLHQKTKEEYEKLEKMKFSNFGQILDKLNTELDNLKTLEKNIVEBQTNYINK
VMSDSLTNLTAEVDNLRS

FIGURE 7
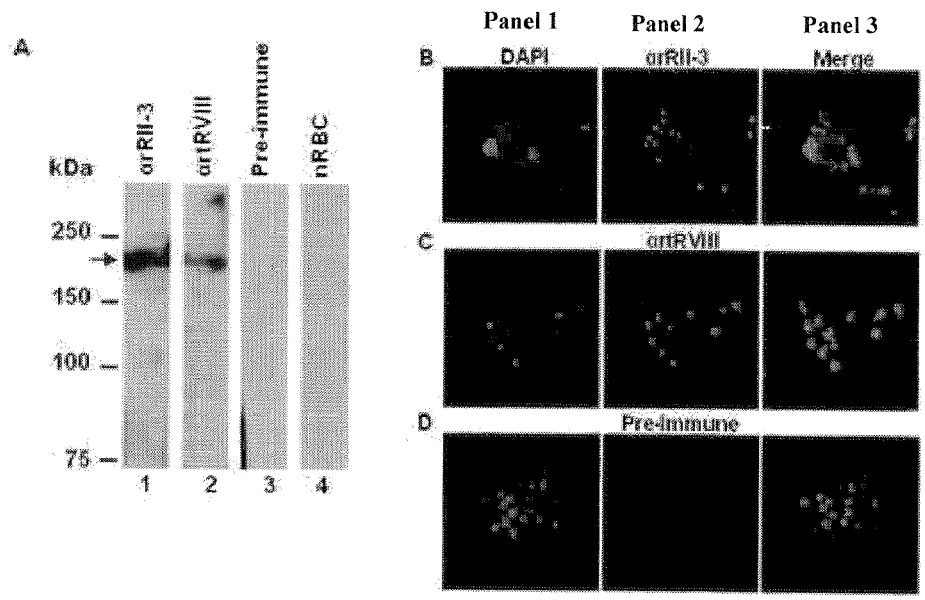
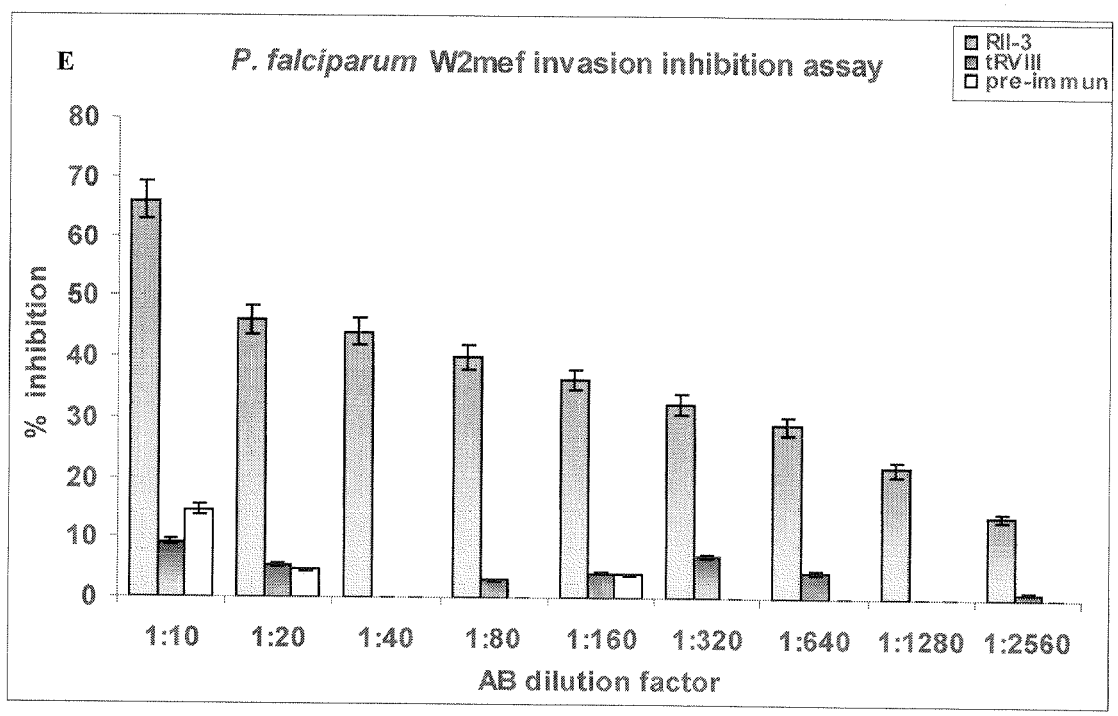

SEQUENCE LISTING

```
<160> NUMBER OF SEQ ID NOS: 43

<210> SEQ ID NO 1
<211> LENGTH: 2001
<212> TYPE: DNA
<213> ORGANISM: Plasmodium falciparum

<400> SEQUENCE: 1
aaagatgtaa taaataataa gatagatata tataaaacaa taagttcttt tatatctact      60
cagaaacaat tatattattt tgaatatata tatataatga ataaaaatac attaaaccta     120
ctttcatata atatacaaaa aacagatata aattctagta gtaaatacac atatacaaaa     180
tctcattttt taaaagataa tcatatattg ttatctaaat attatactgc caaatttatt     240
gatatcctaa ataaaacata ttattataat ttatataaaa ataaaattct tttattcaat     300
aaatatatta taaagcttag aaacgattta aaagaatatg catttaaatc tatacaattt     360
attcaagata aaatcaaaaa acataaagat gaattatcca tagaaaatat attacaagaa     420
gttaataata tatatataaa atatgatact tcgataaatg aaatatctaa atataacaat     480
ttaattatta atactgattt acaaatagta caacaaaaac ttttagaaat caaacaaaaa     540
aaaaatgata ttacacacaa agtacaactt ataaatcata tatataaaaa tatacatgat     600
gaaatattaa acaaaaaaaa taatgaaata acaaagatta ttataaataa tataaaagat     660
cataaaaaag atttacaaga tctcttacta tttatacaac aaatcaaaca atataatata     720
ttaacagatc ataaaattac acaatgtaat aattattata aggaaatcat aaaaatgaaa     780
gaagatataa atcatattca tatatatata caaccaattc taaataattt acacacatta     840
aaacaagtac aaaataataa aatcaaatat gaagagcaca tcaaacaaat attacaaaaa     900
atttatgata aaaaggaatc tttaaaaaaa attattctct taaagatgaa agcacaatta     960
gacattaccc tcctcgatga cttaatacaa aagcaaacaa aaaaacaaac acaaacacaa    1020
acacaaacac aaaaacaaac actaatacaa aataatgaga cgattcaact tatttctgga    1080
```

```
caagaagata aacatgaatc caatccattt aatcatatac aaacctatat tcaacaaaaa   1140
gatacacaaa ataaaaacat ccaaaatctt cttaaatcct tgtataatgg aaatattaac   1200
acattcatag acacaatttc taaatatata ttaaaacaaa aagatataga attaacacaa   1260
cacgtttata cagacgaaaa aattaatgat tatcttgaag aaataaaaaa tgaacaaaac   1320
aaaatagata agaccatcga cgatataaaa atacaagaaa cattaaaaca ataactcat    1380 attgttaaca atataaaaac catcaaaaag gatttgctca aagaatttat tcaacattta   1440
ataaaatata tgaacgaaag atatcagaat atgcaacagg gttataataa tttaacaaat   1500
tatattaatc aatatgaaga agaaaataat aatatgaaac aatatattac taccatacga   1560
aatatccaaa aaatatatta tgataatata tatgctaagg aaaaggaaat tcgctcggga   1620
caatattata aggattttat cacatcaagg aaaaatattt ataatataag ggaaaatata   1680
tccaaaaatg tagatatgat aaaaaatgaa gaaaagaaga aaatacagaa ttgtgtagat   1740
aaatataatt ctataaaaca atatgtaaaa atgcttaaaa atggagacac acaagatgaa   1800
aataataata ataataatga tatatacgac aagttaattg tccccttga ttcaataaaa    1860 caaaatatcg ataaatacaa cacagaacat aattttataa catttacaaa taaaataaat   1920
acacataata agaagaacca agaaatgatg gaagaattca tatatgcata taaaaggtta   1980
aaaattttaa aaatattaaa t                                             2001
```

<210> SEQ ID NO 2
<211> LENGTH: 667
<212> TYPE: PRT
<213> ORGANISM: Plasmodium falciparum

<400> SEQUENCE: 2

```
Lys Asp Val Ile Asn Asn Lys Ile Asp Ile Tyr Lys Thr Ile Ser Ser
1               5                   10                  15

Phe Ile Ser Thr Gln Lys Gln Leu Tyr Tyr Phe Glu Tyr Ile Tyr Ile
            20                  25                  30

Met Asn Lys Asn Thr Leu Asn Leu Leu Ser Tyr Asn Ile Gln Lys Thr
        35                  40                  45

Asp Ile Asn Ser Ser Lys Tyr Thr Tyr Thr Lys Ser His Phe Leu
    50                  55                  60

Lys Asp Asn His Ile Leu Leu Ser Lys Tyr Tyr Thr Ala Lys Phe Ile
65                  70                  75                  80

Asp Ile Leu Asn Lys Thr Tyr Tyr Tyr Asn Leu Tyr Lys Asn Lys Ile
                85                  90                  95

Leu Leu Phe Asn Lys Tyr Ile Ile Lys Leu Arg Asn Asp Leu Lys Glu
            100                 105                 110

Tyr Ala Phe Lys Ser Ile Gln Phe Ile Gln Asp Lys Ile Lys Lys His
        115                 120                 125

Lys Asp Glu Leu Ser Ile Glu Asn Ile Leu Gln Glu Val Asn Asn Ile
    130                 135                 140

Tyr Ile Lys Tyr Asp Thr Ser Ile Asn Glu Ile Ser Lys Tyr Asn Asn
145                 150                 155                 160

Leu Ile Ile Asn Thr Asp Leu Gln Ile Val Gln Gln Lys Leu Leu Glu
                165                 170                 175

Ile Lys Gln Lys Lys Asn Asp Ile Thr His Lys Val Gln Leu Ile Asn
            180                 185                 190

His Ile Tyr Lys Asn Ile His Asp Glu Ile Leu Asn Lys Lys Asn Asn
        195                 200                 205
```

```
Glu Ile Thr Lys Ile Ile Ile Asn Asn Ile Lys Asp His Lys Lys Asp
        210                 215                 220

Leu Gln Asp Leu Leu Leu Phe Ile Gln Gln Ile Lys Gln Tyr Asn Ile
225                 230                 235                 240

Leu Thr Asp His Lys Ile Thr Gln Cys Asn Asn Tyr Tyr Lys Glu Ile
                245                 250                 255

Ile Lys Met Lys Glu Asp Ile Asn His Ile His Ile Tyr Ile Gln Pro
                260                 265                 270

Ile Leu Asn Asn Leu His Thr Leu Lys Gln Val Gln Asn Asn Lys Ile
            275                 280                 285

Lys Tyr Glu Glu His Ile Lys Gln Ile Leu Gln Lys Ile Tyr Asp Lys
        290                 295                 300

Lys Glu Ser Leu Lys Lys Ile Ile Leu Leu Lys Asp Glu Ala Gln Leu
305                 310                 315                 320

Asp Ile Thr Leu Leu Asp Asp Leu Ile Gln Lys Gln Thr Lys Lys Gln
                325                 330                 335

Thr Gln Thr Gln Thr Gln Thr Gln Lys Gln Thr Leu Ile Gln Asn Asn
                340                 345                 350

Glu Thr Ile Gln Leu Ile Ser Gly Gln Glu Asp Lys His Glu Ser Asn
        355                 360                 365

Pro Phe Asn His Ile Gln Thr Tyr Ile Gln Gln Lys Asp Thr Gln Asn
370                 375                 380

Lys Asn Ile Gln Asn Leu Leu Lys Ser Leu Tyr Asn Gly Asn Ile Asn
385                 390                 395                 400

Thr Phe Ile Asp Thr Ile Ser Lys Tyr Ile Leu Lys Gln Lys Asp Ile
                405                 410                 415

Glu Leu Thr Gln His Val Tyr Thr Asp Glu Lys Ile Asn Asp Tyr Leu
            420                 425                 430

Glu Glu Ile Lys Asn Glu Gln Asn Lys Ile Asp Lys Thr Ile Asp Asp
                435                 440                 445

Ile Lys Ile Gln Glu Thr Leu Lys Gln Ile Thr His Ile Val Asn Asn
        450                 455                 460

Ile Lys Thr Ile Lys Lys Asp Leu Leu Lys Glu Phe Ile Gln His Leu
465                 470                 475                 480

Ile Lys Tyr Met Asn Glu Arg Tyr Gln Asn Met Gln Gln Gly Tyr Asn
                485                 490                 495

Asn Leu Thr Asn Tyr Ile Asn Gln Tyr Glu Glu Glu Asn Asn Asn Met
            500                 505                 510

Lys Gln Tyr Ile Thr Thr Ile Arg Asn Ile Gln Lys Ile Tyr Tyr Asp
        515                 520                 525

Asn Ile Tyr Ala Lys Glu Lys Glu Ile Arg Ser Gly Gln Tyr Tyr Lys
530                 535                 540

Asp Phe Ile Thr Ser Arg Lys Asn Ile Tyr Asn Ile Arg Glu Asn Ile
545                 550                 555                 560

Ser Lys Asn Val Asp Met Ile Lys Asn Glu Lys Lys Lys Ile Gln
                565                 570                 575

Asn Cys Val Asp Lys Tyr Asn Ser Ile Lys Gln Tyr Val Lys Met Leu
                580                 585                 590

Lys Asn Gly Asp Thr Gln Asp Glu Asn Asn Asn Asn Asn Asp Ile
            595                 600                 605

Tyr Asp Lys Leu Ile Val Pro Leu Asp Ser Ile Lys Gln Asn Ile Asp
        610                 615                 620

Lys Tyr Asn Thr Glu His Asn Phe Ile Thr Phe Thr Asn Lys Ile Asn
625                 630                 635                 640
```

```
Thr His Asn Lys Lys Asn Gln Glu Met Met Glu Glu Phe Ile Tyr Ala
            645                 650                 655

Tyr Lys Arg Leu Lys Ile Leu Lys Ile Leu Asn
            660                 665

<210> SEQ ID NO 3
<211> LENGTH: 1500
<212> TYPE: DNA
<213> ORGANISM: Plasmodium falciparum

<400> SEQUENCE: 3
aaagatgtaa taataataa gatagatata tataaaacaa taagttcttt tatatctact     60
cagaaacaat tatattattt tgaatatata tataatga ataaaaatac attaaaccta    120
ctttcatata atatacaaaa aacagatata aattctagta gtaaatacac atatacaaaa    180
tctcattttt taaaagataa tcatatattg ttatctaaat attatactgc caaatttatt    240
gatatcctaa ataaaacata ttattataat ttatataaaa ataaaattct tttattcaat    300
aaatatatta taaagcttag aaacgattta aaagaatatg catttaaatc tatacaattt    360
attcaagata aaatcaaaaa acataaagat gaattatcca tagaaaatat attacaagaa    420
gttaataata tatatataaa atatgatact tcgataaatg aaatatctaa atataacaat    480
ttaattatta atactgattt acaaatagta caacaaaaac ttttagaaat caaacaaaaa    540
aaaaatgata ttcacacaa agtacaactt ataaatcata tatataaaaa tatacatgat    600
gaaatattaa acaaaaaaaa taatgaaata acaaagatta ttataaataa tataaaagat    660
cataaaaaag atttacaaga tctcttacta tttatacaac aaatcaaaca atataatata    720
ttaacagatc ataaaattac acaatgtaat aattattata aggaaatcat aaaaatgaaa    780
gaagatataa atcatattca tatatatata caaccaattc taaataattt acacacatta    840
aaacaagtac aaaataataa aatcaaatat gaagagcaca tcaaacaaat attacaaaaa    900
atttatgata aaaaggaatc tttaaaaaaa attattctct taaaagatga agcacaatta    960
gacattaccc tcctcgatga cttaatacaa agcaaacaa aaaaacaaac acaaacacaa   1020
acacaaacac aaaaacaaac actaatacaa ataatgaga cgattcaact tatttctgga   1080
caagaagata acatgaatc caatccattt aatcatatac aaacctatat tcaacaaaaa   1140
gatacacaaa ataaaacat ccaaaatctt cttaaatcct tgtataatgg aaatattaac   1200
acattcatag acacaatttc taaatatata ttaaaacaaa aagatataga attaacacaa   1260 cacgttata cagacgaaaa aattaatgat tatcttgaag aaataaaaaa tgaacaaaac   1320
aaaatagata agaccatcga cgatataaaa atacaagaaa cattaaaaca ataactcat   1380 attgttaaca atataaaaac catcaaaaag gatttgctca aagaatttat tcaacattta   1440
ataaaatata tgaacgaaag atatcagaat atgcaacagg gttataataa tttaacaaat   1500

<210> SEQ ID NO 4
<211> LENGTH: 500
<212> TYPE: PRT
<213> ORGANISM: Plasmodium falciparum

<400> SEQUENCE: 4

Lys Asp Val Ile Asn Asn Lys Ile Asp Ile Tyr Lys Thr Ile Ser Ser
  1               5                  10                  15

Phe Ile Ser Thr Gln Lys Gln Leu Tyr Tyr Phe Glu Tyr Ile Tyr Ile
             20                  25                  30

Met Asn Lys Asn Thr Leu Asn Leu Ser Tyr Asn Ile Gln Lys Thr
         35                  40                  45
```

-continued

```
Asp Ile Asn Ser Ser Lys Tyr Thr Tyr Thr Lys Ser His Phe Leu
         50                  55                  60
Lys Asp Asn His Ile Leu Leu Ser Lys Tyr Tyr Thr Ala Lys Phe Ile
 65                  70                  75                  80
Asp Ile Leu Asn Lys Thr Tyr Tyr Asn Leu Tyr Lys Asn Lys Ile
                 85                  90                  95
Leu Leu Phe Asn Lys Tyr Ile Ile Lys Leu Arg Asn Asp Leu Lys Glu
                100                 105                 110
Tyr Ala Phe Lys Ser Ile Gln Phe Ile Gln Asp Lys Ile Lys Lys His
                115                 120                 125
Lys Asp Glu Leu Ser Ile Glu Asn Ile Leu Gln Glu Val Asn Asn Ile
130                 135                 140
Tyr Ile Lys Tyr Asp Thr Ser Ile Asn Glu Ile Ser Lys Tyr Asn Asn
145                 150                 155                 160
Leu Ile Ile Asn Thr Asp Leu Gln Ile Val Gln Gln Lys Leu Leu Glu
                165                 170                 175
Ile Lys Gln Lys Lys Asn Asp Ile Thr His Lys Val Gln Leu Ile Asn
                180                 185                 190
His Ile Tyr Lys Asn Ile His Asp Glu Ile Leu Asn Lys Lys Asn Asn
                195                 200                 205
Glu Ile Thr Lys Ile Ile Asn Asn Ile Lys Asp His Lys Lys Asp
210                 215                 220
Leu Gln Asp Leu Leu Leu Phe Ile Gln Gln Ile Lys Gln Tyr Asn Ile
225                 230                 235                 240
Leu Thr Asp His Lys Ile Thr Gln Cys Asn Asn Tyr Tyr Lys Glu Ile
                245                 250                 255
Ile Lys Met Lys Glu Asp Ile Asn His Ile His Ile Tyr Ile Gln Pro
                260                 265                 270
Ile Leu Asn Asn Leu His Thr Leu Lys Gln Val Gln Asn Asn Lys Ile
                275                 280                 285
Lys Tyr Glu Glu His Ile Lys Gln Ile Leu Gln Lys Ile Tyr Asp Lys
                290                 295                 300
Lys Glu Ser Leu Lys Lys Ile Ile Leu Leu Lys Asp Glu Ala Gln Leu
305                 310                 315                 320
Asp Ile Thr Leu Leu Asp Asp Leu Ile Gln Lys Gln Thr Lys Lys Gln
                325                 330                 335
Thr Gln Thr Gln Thr Gln Thr Gln Lys Gln Thr Leu Ile Gln Asn Asn
                340                 345                 350
Glu Thr Ile Gln Leu Ile Ser Gly Gln Glu Asp Lys His Glu Ser Asn
                355                 360                 365
Pro Phe Asn His Ile Gln Thr Tyr Ile Gln Gln Lys Asp Thr Gln Asn
                370                 375                 380
Lys Asn Ile Gln Asn Leu Leu Lys Ser Leu Tyr Asn Gly Asn Ile Asn
385                 390                 395                 400
Thr Phe Ile Asp Thr Ile Ser Lys Tyr Ile Leu Lys Gln Lys Asp Ile
                405                 410                 415
Glu Leu Thr Gln His Val Tyr Thr Asp Glu Lys Ile Asn Asp Tyr Leu
                420                 425                 430
Glu Glu Ile Lys Asn Glu Gln Asn Lys Ile Asp Lys Thr Ile Asp Asp
                435                 440                 445
Ile Lys Ile Gln Glu Thr Leu Lys Gln Ile Thr His Ile Val Asn Asn
                450                 455                 460
Ile Lys Thr Ile Lys Lys Asp Leu Leu Lys Glu Phe Ile Gln His Leu
465                 470                 475                 480
```

Ile Lys Tyr Met Asn Glu Arg Tyr Gln Asn Met Gln Gln Gly Tyr Asn
            485                 490                 495

Asn Leu Thr Asn
            500

<210> SEQ ID NO 5
<211> LENGTH: 1503
<212> TYPE: DNA
<213> ORGANISM: Plasmodium falciparum

<400> SEQUENCE: 5

```
ttacaaatag tacaacaaaa acttttagaa atcaaacaaa aaaaaaatga tattacacac      60
aaagtacaac ttataaatca tatatataaa aatatacatg atgaaatatt aaacaaaaaa     120
aataatgaaa taacaaagat tattataaat aatataaaag atcataaaaa agatttacaa     180
gatctcttac tatttataca acaaatcaaa caatataata tattaacaga tcataaaatt     240
acacaatgta ataattatta taggaaaatc ataaaaatga aagaagatat aaatcatatt     300
catatatata taaccaat tctaaataat ttacacacat aaaacaagt acaaaataat     360
aaaatcaaat atgaagagca catcaaacaa atattacaaa aatttatga taaaaaggaa     420
tctttaaaaa aaattattct cttaaaagat gaagcacaat tagacattac cctcctcgat     480
gacttaatac aaaagcaaac aaaaaaacaa acacaaacac aaacacaaac acaaaaacaa     540
acactaatac aaaataatga gacgattcaa cttatttctg gacaagaaga taaacatgaa     600
tccaatccat ttaatcatat acaaacctat attcaacaaa aagatacaca aaataaaaac     660
atccaaaatc ttcttaaatc cttgtataat ggaaatatta acacattcat agacacaatt     720
tctaaatata tattaaaaca aaaagatata gaattaacac aacacgttta tacagacgaa     780
aaaattaatg attatcttga agaaataaaa aatgaacaaa acaaaataga taagaccatc     840
gacgatataa aaatacaaga aacattaaaa caaataactc atattgttaa caatataaaa     900
accatcaaaa aggatttgct caaagaattt attcaacatt taataaaata tatgaacgaa     960
agatatcaga atatgcaaca gggttataat aatttaacaa attatattaa tcaatatgaa    1020
gaagaaaata ataatatgaa acaatatatt actaccatac gaaatatcca aaaaatatat    1080
tatgataata tatatgctaa ggaaaaggaa attcgctcgg gacaatatta taaggatttt    1140
atcacatcaa ggaaaaatat ttataatata agggaaaata tatccaaaaa tgtagatatg    1200
ataaaaaatg aagaaagaa gaaaatacag aattgtgtag ataaatataa ttctataaaa    1260
caatatgtaa aaatgcttaa aaatggagac acacaagatg aaaataataa taataataat    1320
gatatatacg acaagttaat tgtcccccctt gattcaataa acaaaatat cgataaatac    1380
aacacagaac ataattttat aacatttaca aataaaataa atacacataa taagaagaac    1440
caagaaatga tggaagaatt catatatgca tataaaaggt taaaaatttt aaaaatatta    1500
aat                                                                  1503
```

<210> SEQ ID NO 6
<211> LENGTH: 501
<212> TYPE: PRT
<213> ORGANISM: Plasmodium falciparum

<400> SEQUENCE: 6

Leu Gln Ile Val Gln Gln Lys Leu Leu Glu Ile Lys Gln Lys Asn
1               5                   10                  15

Asp Ile Thr His Lys Val Gln Leu Ile Asn His Ile Tyr Lys Asn Ile
            20                  25                  30

-continued

His Asp Glu Ile Leu Asn Lys Asn Asn Glu Ile Thr Lys Ile Ile
      35                  40                  45

Ile Asn Asn Ile Lys Asp His Lys Lys Asp Leu Gln Asp Leu Leu
 50                  55                  60

Phe Ile Gln Gln Ile Lys Gln Tyr Asn Ile Leu Thr Asp His Lys Ile
65                  70                  75                  80

Thr Gln Cys Asn Asn Tyr Tyr Lys Glu Ile Ile Lys Met Lys Glu Asp
                85                  90                  95

Ile Asn His Ile His Ile Tyr Ile Gln Pro Ile Leu Asn Asn Leu His
              100                 105                 110

Thr Leu Lys Gln Val Gln Asn Asn Lys Ile Lys Tyr Glu Glu His Ile
          115                 120                 125

Lys Gln Ile Leu Gln Lys Ile Tyr Asp Lys Lys Glu Ser Leu Lys Lys
      130                 135                 140

Ile Ile Leu Leu Lys Asp Glu Ala Gln Leu Asp Ile Thr Leu Leu Asp
145                 150                 155                 160

Asp Leu Ile Gln Lys Gln Thr Lys Lys Gln Thr Gln Thr Gln Thr Gln
                165                 170                 175

Thr Gln Lys Gln Thr Leu Ile Gln Asn Asn Glu Thr Ile Gln Leu Ile
              180                 185                 190

Ser Gly Gln Glu Asp Lys His Glu Ser Asn Pro Phe Asn His Ile Gln
          195                 200                 205

Thr Tyr Ile Gln Gln Lys Asp Thr Gln Asn Lys Asn Ile Gln Asn Leu
      210                 215                 220

Leu Lys Ser Leu Tyr Asn Gly Asn Ile Asn Thr Phe Ile Asp Thr Ile
225                 230                 235                 240

Ser Lys Tyr Ile Leu Lys Gln Lys Asp Ile Glu Leu Thr Gln His Val
                245                 250                 255

Tyr Thr Asp Glu Lys Ile Asn Asp Tyr Leu Glu Glu Ile Lys Asn Glu
              260                 265                 270

Gln Asn Lys Ile Asp Lys Thr Ile Asp Asp Ile Lys Ile Gln Glu Thr
          275                 280                 285

Leu Lys Gln Ile Thr His Ile Val Asn Asn Ile Lys Thr Ile Lys Lys
      290                 295                 300

Asp Leu Leu Lys Glu Phe Ile Gln His Leu Ile Lys Tyr Met Asn Glu
305                 310                 315                 320

Arg Tyr Gln Asn Met Gln Gln Gly Tyr Asn Asn Leu Thr Asn Tyr Ile
                325                 330                 335

Asn Gln Tyr Glu Glu Asn Asn Met Lys Gln Tyr Ile Thr Thr
              340                 345                 350

Ile Arg Asn Ile Gln Lys Ile Tyr Tyr Asp Asn Ile Tyr Ala Lys Glu
          355                 360                 365

Lys Glu Ile Arg Ser Gly Gln Tyr Tyr Lys Asp Phe Ile Thr Ser Arg
      370                 375                 380

Lys Asn Ile Tyr Asn Ile Arg Glu Asn Ile Ser Lys Asn Val Asp Met
385                 390                 395                 400

Ile Lys Asn Glu Glu Lys Lys Ile Gln Asn Cys Val Asp Lys Tyr
                405                 410                 415

Asn Ser Ile Lys Gln Tyr Val Lys Met Leu Lys Asn Gly Asp Thr Gln
              420                 425                 430

Asp Glu Asn Asn Asn Asn Asn Asn Asp Ile Tyr Asp Lys Leu Ile Val
          435                 440                 445

Pro Leu Asp Ser Ile Lys Gln Asn Ile Asp Lys Tyr Asn Thr Glu His
450                 455                 460

-continued

```
Asn Phe Ile Thr Phe Thr Asn Lys Ile Asn Thr His Asn Lys Lys Asn
465                 470                 475                 480

Gln Glu Met Met Glu Glu Phe Ile Tyr Ala Tyr Lys Arg Leu Lys Ile
            485                 490                 495

Leu Lys Ile Leu Asn
            500
```

<210> SEQ ID NO 7
<211> LENGTH: 1002
<212> TYPE: DNA
<213> ORGANISM: Plasmodium falciparum

<400> SEQUENCE: 7

```
ttacaaatag tacaacaaaa acttttagaa atcaaacaaa aaaaaaatga tattacacac    60
aaagtacaac ttataaatca tatatataaa aatatacatg atgaaatatt aaacaaaaaa   120
aataatgaaa taacaaagat tattataaat aatataaaag atcataaaaa agatttacaa   180
gatctcttac tatttataca acaaatcaaa caatataata tattaacaga tcataaaatt   240
acacaatgta ataattatta taaggaaatc ataaaaatga agaagatat aaatcatatt    300
catatatata tacaaccaat tctaaataat ttacacacat taaaacaagt acaaataat    360
aaaatcaaat atgaagagca catcaaacaa atattacaaa aatttatga taaaaggaa     420
tctttaaaaa aaattattct cttaaaagat gaagcacaat tagacattac cctcctcgat   480
gacttaatac aaaagcaaac aaaaaaacaa acacaaacac aaacacaaac acaaaaacaa   540
acactaatac aaaataatga gacgattcaa cttatttctg acaagaaga taaacatgaa    600
tccaatccat ttaatcatat acaaacctat attcaacaaa aagatacaca aataaaaac    660
atccaaaatc ttcttaaatc cttgtataat ggaaatatta acacattcat agacacaatt   720
tctaaatata tattaaaaca aaaagatata gaattaacac aacacgttta tacagacgaa   780
aaaattaatg attatcttga agaaatcaaa aatgaacaaa acaaaataga taagaccatc   840
gacgatataa aaatacaaga aacattaaaa caaataactc atattgttaa caatataaaa   900
accatcaaaa aggatttgct caaagaattt attcaacatt taataaaata tatgaacgaa   960
agatatcaga atatgcaaca gggttataat aatttaacaa at                    1002
```

<210> SEQ ID NO 8
<211> LENGTH: 334
<212> TYPE: PRT
<213> ORGANISM: Plasmodium falciparum

<400> SEQUENCE: 8

```
Leu Gln Ile Val Gln Gln Lys Leu Leu Glu Ile Lys Gln Lys Lys Asn
1               5                   10                  15

Asp Ile Thr His Lys Val Gln Leu Ile Asn His Ile Tyr Lys Asn Ile
            20                  25                  30

His Asp Glu Ile Leu Asn Lys Lys Asn Asn Glu Ile Thr Lys Ile Ile
        35                  40                  45

Ile Asn Asn Ile Lys Asp His Lys Lys Asp Leu Gln Asp Leu Leu Leu
    50                  55                  60

Phe Ile Gln Gln Ile Lys Gln Tyr Asn Ile Leu Thr Asp His Lys Ile
65                  70                  75                  80

Thr Gln Cys Asn Asn Tyr Tyr Lys Glu Ile Ile Lys Met Lys Glu Asp
                85                  90                  95

Ile Asn His Ile His Ile Tyr Ile Gln Pro Ile Leu Asn Asn Leu His
            100                 105                 110
```

-continued

```
Thr Leu Lys Gln Val Gln Asn Lys Ile Lys Tyr Glu Glu His Ile
    115                 120                 125

Lys Gln Ile Leu Gln Lys Ile Tyr Asp Lys Lys Ser Leu Lys Lys
130                 135                 140

Ile Ile Leu Leu Lys Asp Glu Ala Gln Leu Asp Ile Thr Leu Leu Asp
145                 150                 155                 160

Asp Leu Ile Gln Lys Gln Thr Lys Lys Gln Thr Gln Thr Gln
            165                 170                 175

Thr Gln Lys Gln Thr Leu Ile Gln Asn Asn Glu Thr Ile Gln Leu Ile
            180                 185                 190

Ser Gly Gln Glu Asp Lys His Glu Ser Asn Pro Phe Asn His Ile Gln
    195                 200                 205

Thr Tyr Ile Gln Gln Lys Asp Thr Gln Asn Lys Asn Ile Gln Asn Leu
    210                 215                 220

Leu Lys Ser Leu Tyr Asn Gly Asn Ile Asn Thr Phe Ile Asp Thr Ile
225                 230                 235                 240

Ser Lys Tyr Ile Leu Lys Gln Lys Asp Ile Glu Leu Thr Gln His Val
            245                 250                 255

Tyr Thr Asp Glu Lys Ile Asn Asp Tyr Leu Glu Glu Ile Lys Asn Glu
            260                 265                 270

Gln Asn Lys Ile Asp Lys Thr Ile Asp Asp Ile Lys Ile Gln Glu Thr
    275                 280                 285

Leu Lys Gln Ile Thr His Ile Val Asn Asn Ile Lys Thr Ile Lys Lys
    290                 295                 300

Asp Leu Leu Lys Glu Phe Ile Gln His Leu Ile Lys Tyr Met Asn Glu
305                 310                 315                 320

Arg Tyr Gln Asn Met Gln Gln Gly Tyr Asn Asn Leu Thr Asn
            325                 330

<210> SEQ ID NO 9
<211> LENGTH: 30
<212> TYPE: DNA
<213> ORGANISM: artificial
<220> FEATURE:
<223> OTHER INFORMATION: Forward primer PfRH1-R-I

<400> SEQUENCE: 9
gaccagctgg aatttagcca tgaacaggaa                                    30

<210> SEQ ID NO 10
<211> LENGTH: 30
<212> TYPE: DNA
<213> ORGANISM: artificial
<220> FEATURE:
<223> OTHER INFORMATION: Reverse primer PfRH1-R-I

<400> SEQUENCE: 10
aacgggccct tttgtttgct tttgtattaa                                    30

<210> SEQ ID NO 11
<211> LENGTH: 30
<212> TYPE: DNA
<213> ORGANISM: artificial
<220> FEATURE:
<223> OTHER INFORMATION: Forward primer PfRH1-RII

<400> SEQUENCE: 11
gaccagctga aagatgtaat aaataataag                                    30
```

```
<210> SEQ ID NO 12
<211> LENGTH: 30
<212> TYPE: DNA
<213> ORGANISM: artificial
<220> FEATURE:
<223> OTHER INFORMATION: Reverse primer PfRH1-R-II

<400> SEQUENCE: 12
aacgggccca tttaatattt ttaaaatttt                                30

<210> SEQ ID NO 13
<211> LENGTH: 33
<212> TYPE: DNA
<213> ORGANISM: artificial
<220> FEATURE:
<223> OTHER INFORMATION: Forward primer PfRH1-R-III

<400> SEQUENCE: 13
tctcgtcagc tgctaataca aaataatgag acg                            33

<210> SEQ ID NO 14
<211> LENGTH: 33
<212> TYPE: DNA
<213> ORGANISM: artificial
<220> FEATURE:
<223> OTHER INFORMATION: Reverse primer PfRH1-R-III

<400> SEQUENCE: 14
acgatggggc cctatatcgt caaaatgttt tgt                            33

<210> SEQ ID NO 15
<211> LENGTH: 30
<212> TYPE: DNA
<213> ORGANISM: artificial
<220> FEATURE:
<223> OTHER INFORMATION: Forward primer PfRH1-R-IV

<400> SEQUENCE: 15
gaccagctga tatccttaaa agcttgtgaa                                30

<210> SEQ ID NO 16
<211> LENGTH: 30
<212> TYPE: DNA
<213> ORGANISM: artificial
<220> FEATURE:
<223> OTHER INFORMATION: Reverse primer PfRH1-R-IV

<400> SEQUENCE: 16
aacgggccct ttagatttgt ttacatctat                                30

<210> SEQ ID NO 17
<211> LENGTH: 30
<212> TYPE: DNA
<213> ORGANISM: artificial
<220> FEATURE:
<223> OTHER INFORMATION: Forward primer PfRH1-R-V

<400> SEQUENCE: 17
gaccagctgt accatgctga tgatacacgt                                30

<210> SEQ ID NO 18
<211> LENGTH: 30
<212> TYPE: DNA
<213> ORGANISM: artificial
<220> FEATURE:
<223> OTHER INFORMATION: Reverse primer PfRH1-R-V
```

```
<400> SEQUENCE: 18
aacgggccct ataaaaacat tatatatttc                                              30

<210> SEQ ID NO 19
<211> LENGTH: 30
<212> TYPE: DNA
<213> ORGANISM: artificial
<220> FEATURE:
<223> OTHER INFORMATION: Forward primer PfRH1-R-VI

<400> SEQUENCE: 19
gaccagctga ataatgctca actatatttt                                              30

<210> SEQ ID NO 20
<211> LENGTH: 30
<212> TYPE: DNA
<213> ORGANISM: artificial
<220> FEATURE:
<223> OTHER INFORMATION: Reverse primer PfRH1-R-VI

<400> SEQUENCE: 20
aacgggccca ttcatttgtt ctaatttgtt                                              30

<210> SEQ ID NO 21
<211> LENGTH: 30
<212> TYPE: DNA
<213> ORGANISM: artificial
<220> FEATURE:
<223> OTHER INFORMATION: Forward primer PfRH1-R-VII

<400> SEQUENCE: 21
gaccagctgc aatcatataa tttaatacaa                                              30

<210> SEQ ID NO 22
<211> LENGTH: 29
<212> TYPE: DNA
<213> ORGANISM: artificial
<220> FEATURE:
<223> OTHER INFORMATION: Reverse primer PfRH1-R-VII

<400> SEQUENCE: 22
aacgggcccg atgttggtta tatttcttg                                               29

<210> SEQ ID NO 23
<211> LENGTH: 30
<212> TYPE: DNA
<213> ORGANISM: artificial
<220> FEATURE:
<223> OTHER INFORMATION: Forward primer PfRH1-R-VIII

<400> SEQUENCE: 23
gaccagctga caataattaa tcaaagtata                                              30

<210> SEQ ID NO 24
<211> LENGTH: 30
<212> TYPE: DNA
<213> ORGANISM: artificial
<220> FEATURE:
<223> OTHER INFORMATION: Reverse primer PfRH1-R-VIII

<400> SEQUENCE: 24
aacgggccca ttttttttttt tgttcaattc                                             30
```

```
<210> SEQ ID NO 25
<211> LENGTH: 33
<212> TYPE: DNA
<213> ORGANISM: artificial
<220> FEATURE:
<223> OTHER INFORMATION: Forward primer PfRH1-R-II-1

<400> SEQUENCE: 25
tctcgtcagc tgaaagatgt aataaataat aag                              33

<210> SEQ ID NO 26
<211> LENGTH: 30
<212> TYPE: DNA
<213> ORGANISM: artificial
<220> FEATURE:
<223> OTHER INFORMATION: Reverse primer PfRH1-R-II-1

<400> SEQUENCE: 26
aacgggccca tttgttaaat tattataacc                                  30

<210> SEQ ID NO 27
<211> LENGTH: 30
<212> TYPE: DNA
<213> ORGANISM: artificial
<220> FEATURE:
<223> OTHER INFORMATION: Forward primer PfRH1-R-II-2

<400> SEQUENCE: 27
gaccagctgt tacaaatagt acaacaaaaa                                  30

<210> SEQ ID NO 28
<211> LENGTH: 30
<212> TYPE: DNA
<213> ORGANISM: artificial
<220> FEATURE:
<223> OTHER INFORMATION: Reverse primer PfRH1-R-II-2

<400> SEQUENCE: 28
aacgggccca tttaatatttt ttaaaattttt                                30

<210> SEQ ID NO 29
<211> LENGTH: 30
<212> TYPE: DNA
<213> ORGANISM: artificial
<220> FEATURE:
<223> OTHER INFORMATION: Forward primer PfRH1-R-II-3

<400> SEQUENCE: 29
gaccagctgt tacaaatagt acaacaaaaa                                  30

<210> SEQ ID NO 30
<211> LENGTH: 30
<212> TYPE: DNA
<213> ORGANISM: artificial
<220> FEATURE:
<223> OTHER INFORMATION: Reverse primer PfRH1-R-II-3

<400> SEQUENCE: 30
aacgggccca tttgttaaat tattataacc                                  30

<210> SEQ ID NO 31
<211> LENGTH: 30
<212> TYPE: DNA
<213> ORGANISM: artificial
<220> FEATURE:
<223> OTHER INFORMATION: Universal forward primer PfRH1-RI to RVIII
```

```
<400> SEQUENCE: 31
cgtatactcg agatgggggg gactgccgcc                                            30

<210> SEQ ID NO 32
<211> LENGTH: 29
<212> TYPE: DNA
<213> ORGANISM: artificial
<220> FEATURE:
<223> OTHER INFORMATION: Universal reverse primer PfRH1-RI to RVIII

<400> SEQUENCE: 32
cgtataggat ccaagtaaaa caagggctg                                             29

<210> SEQ ID NO 33
<211> LENGTH: 30
<212> TYPE: DNA
<213> ORGANISM: artificial
<220> FEATURE:
<223> OTHER INFORMATION: Forward primer PfRH1-R-II-3 for pET24a+

<400> SEQUENCE: 33
gaccatatgt tacaaatagt acaacaaaaa                                            30

<210> SEQ ID NO 34
<211> LENGTH: 30
<212> TYPE: DNA
<213> ORGANISM: artificial
<220> FEATURE:
<223> OTHER INFORMATION: Reverse primer PfRH1-R-II-3 for pET24a+

<400> SEQUENCE: 34
aacctcgaga tttgttaaat tattataacc                                            30

<210> SEQ ID NO 35
<211> LENGTH: 30
<212> TYPE: DNA
<213> ORGANISM: artificial
<220> FEATURE:
<223> OTHER INFORMATION: Forward primer PfRH1-R-VIII for pET24a+

<400> SEQUENCE: 35
gacgaattca taaatgaaga agctctacaa                                            30

<210> SEQ ID NO 36
<211> LENGTH: 30
<212> TYPE: DNA
<213> ORGANISM: artificial
<220> FEATURE:
<223> OTHER INFORMATION: Reverse primer PfRH1-R-VIII for pET24a+

<400> SEQUENCE: 36
aacctcgaga tttttttttt tgttcaattc                                            30

<210> SEQ ID NO 37
<211> LENGTH: 1002
<212> TYPE: DNA
<213> ORGANISM: Plasmodium falciparum

<400> SEQUENCE: 37
ataaatgaag aagctctaca atttcacagg ctctatggac acaatcttat aagtgaagat           60
gacaaaaata atttggtaca tattataaaa gaacaaaaga atatatatac acaaaaggaa          120
atagatattt ctaaaataat taacatgtt aaaaaggat tatattcatt gaatgaacat            180
gatatgaatc atgatacaca tatgaatata ataaatgaac atataaataa taatattta           240
```

```
caaccataca cacaattaat aaacatgata aagatattg ataatgtttt tataaaaata    300
caaaataata aattcgaaca aatacaaaaa tatatagaaa ttattaaatc tttagaacaa    360
ttaaataaaa atataaacac agataatttta aataaattaa aagatacaca aaacaaatta    420
ataaatatag aaacagaaat gaaacataaa caaaaacaat taataaacaa aatgaatgat    480
atagaaaagg ataatattac agatcaatat atgcatgatg ttcagcaaaa tatatttgaa    540
cctataacat taaaaatgaa tgaatataat acattattaa atgataatca taataataat    600
ataaataatg aacatcaatt taatcattta aatagtcttc atacaaaaat atttagtcat    660
aattataata aagaacaaca acaagaatat ataaccaaca tcatgcaaag aattgatgta    720
ttcataaatg atttagatac ttaccaatat gaatattatt tttatgaatg gaatcaagaa    780
tataaacaaa tagacaaaaa taaaataaat caacatataa acaatattaa aaataatcta    840
attcatgtta agaaacaatt tgaacacacc ttagaaaata taaaaaataa tgaaaatatt    900
ttcgacaaca tacaattgaa aaaaaaagat attgacgata ttattataaa cattaataat    960
acaaaagaaa catatctaaa agaattgaac aaaaaaaaaa at                      1002
```

<210> SEQ ID NO 38
<211> LENGTH: 332
<212> TYPE: PRT
<213> ORGANISM: Plasmodium falciparum

<400> SEQUENCE: 38

```
Leu Glu Glu Thr Gln Asp Lys Leu Leu Glu Leu Tyr Glu Asn Phe Lys
1               5                  10                  15

Lys Glu Lys Asn Ile Ile Asn Asn Tyr Lys Ile Val His Phe Asn
            20                  25                  30

Lys Leu Lys Glu Ile Glu Asn Ser Leu Glu Thr Tyr Asn Ser Ile Ser
        35                  40                  45

Thr Asn Phe Asn Lys Ile Asn Glu Thr Gln Asn Ile Asp Ile Leu Lys
    50                  55                  60

Asn Glu Phe Asn Asn Ile Lys Thr Lys Ile Asn Asp Lys Val Lys Glu
65                  70                  75                  80

Leu Val His Val Asp Ser Thr Leu Thr Leu Glu Ser Ile Gln Thr Phe
                85                  90                  95

Asn Asn Leu Tyr Gly Asp Leu Met Ser Asn Ile Gln Asp Val Tyr Lys
            100                 105                 110

Tyr Glu Asp Ile Asn Asn Val Glu Leu Lys Lys Val Lys Leu Tyr Ile
        115                 120                 125

Glu Asn Ile Thr Asn Leu Leu Gly Arg Ile Asn Thr Phe Ile Lys Glu
    130                 135                 140

Leu Asp Lys Tyr Gln Asp Glu Asn Asn Gly Ile Asp Lys Tyr Ile Glu
145                 150                 155                 160

Ile Asn Lys Glu Asn Asn Ser Tyr Ile Ile Lys Leu Lys Glu Lys Ala
                165                 170                 175

Asn Asn Leu Lys Glu Asn Phe Ser Lys Leu Leu Gln Asn Ile Lys Arg
            180                 185                 190

Asn Glu Thr Glu Leu Tyr Asn Ile Asn Asn Ile Lys Asp Asp Ile Met
        195                 200                 205

Asn Thr Gly Lys Ser Val Asn Asn Ile Lys Gln Lys Phe Ser Ser Asn
    210                 215                 220

Leu Pro Leu Lys Glu Lys Leu Phe Gln Met Glu Glu Met Leu Leu Asn
225                 230                 235                 240
```

```
Ile Asn Asn Ile Met Asn Glu Thr Lys Arg Ile Ser Asn Thr Ala Ala
                245                 250                 255

Tyr Thr Asn Ile Thr Leu Gln Asp Ile Glu Asn Asn Lys Asn Lys Glu
            260                 265                 270

Asn Asn Asn Met Asn Ile Glu Thr Ile Asp Lys Leu Ile Asp His Ile
        275                 280                 285

Lys Ile His Asn Glu Lys Ile Gln Ala Glu Ile Leu Ile Ile Asp Asp
    290                 295                 300

Ala Lys Arg Lys Val Lys Glu Ile Thr Asp Asn Ile Asn Lys Ala Phe
305                 310                 315                 320

Asn Glu Ile Thr Glu Asn Tyr Asn Asn Glu Asn Asn
            325                 330

<210> SEQ ID NO 39
<211> LENGTH: 332
<212> TYPE: PRT
<213> ORGANISM: Plasmodium falciparum

<400> SEQUENCE: 39

Leu Glu Glu Thr Gln Asp Lys Leu Leu Glu Leu Tyr Glu Asn Phe Lys
1               5                   10                  15

Lys Glu Lys Asn Ile Ile Asn Asn Tyr Lys Ile Val His Phe Asn
            20                  25                  30

Lys Leu Lys Glu Ile Glu Asn Ser Leu Glu Thr Tyr Asn Ser Ile Ser
        35                  40                  45

Thr Asn Phe Asn Lys Ile Asn Glu Thr Gln Asn Ile Asp Ile Leu Lys
    50                  55                  60

Asn Glu Phe Asn Asn Ile Lys Thr Lys Ile Asn Asp Lys Val Lys Glu
65                  70                  75                  80

Leu Val His Val Asp Ser Thr Leu Thr Leu Glu Ser Ile Gln Thr Phe
                85                  90                  95

Asn Asn Leu Tyr Gly Asp Leu Met Ser Asn Ile Gln Asp Val Tyr Lys
            100                 105                 110

Tyr Glu Asp Ile Asn Asn Val Glu Leu Lys Lys Val Lys Leu Tyr Ile
        115                 120                 125

Glu Asn Ile Thr Asn Leu Leu Gly Arg Ile Asn Thr Phe Ile Lys Glu
    130                 135                 140

Leu Asp Lys Tyr Gln Asp Glu Asn Asn Gly Ile Asp Lys Tyr Ile Glu
145                 150                 155                 160

Ile Asn Lys Glu Asn Asn Ser Tyr Ile Ile Lys Leu Lys Glu Lys Ala
                165                 170                 175

Asn Asn Leu Lys Glu Asn Phe Ser Lys Leu Leu Gln Asn Ile Lys Arg
            180                 185                 190

Asn Glu Thr Glu Leu Tyr Asn Ile Asn Asn Ile Lys Asp Asp Ile Met
        195                 200                 205

Asn Thr Gly Lys Ser Val Asn Asn Ile Lys Gln Lys Phe Ser Ser Asn
    210                 215                 220

Leu Pro Leu Lys Glu Lys Leu Phe Gln Met Glu Glu Met Leu Leu Asn
225                 230                 235                 240

Ile Asn Asn Ile Met Asn Glu Thr Lys Arg Ile Ser Asn Thr Asp Ala
                245                 250                 255

Tyr Thr Asn Ile Thr Leu Gln Asp Ile Glu Asn Asn Lys Asn Lys Glu
            260                 265                 270

Asn Asn Asn Met Asn Ile Glu Thr Ile Asp Lys Leu Ile Asp His Ile
        275                 280                 285
```

Lys Ile His Asn Glu Lys Ile Gln Ala Glu Ile Leu Ile Ile Asp Asp
            290                 295                 300

Ala Lys Arg Lys Val Lys Glu Ile Thr Asp Asn Ile Asn Lys Ala Phe
305                 310                 315                 320

Asn Glu Ile Thr Glu Asn Tyr Asn Asn Glu Asn Asn
                325                 330

<210> SEQ ID NO 40
<211> LENGTH: 303
<212> TYPE: PRT
<213> ORGANISM: Plasmodium falciparum

<400> SEQUENCE: 40

Leu Asn Lys Phe Met Gln Asn Glu Thr Phe Lys Lys Asn Ile Asp Asp
1               5                   10                  15

Lys Ile Lys Glu Met Asn Asn Ile Tyr Asp Asn Ile Tyr Ile Ile Leu
            20                  25                  30

Lys Gln Lys Phe Leu Asn Lys Leu Asn Glu Ile Ile Gln Asn His Lys
        35                  40                  45

Asn Lys Gln Glu Thr Lys Leu Asn Thr Thr Ile Gln Glu Leu Leu
50                  55                  60

Gln Leu Leu Lys Asp Ile Lys Glu Ile Gln Thr Lys Gln Ile Asp Thr
65                  70                  75                  80

Lys Ile Asn Thr Phe Asn Met Tyr Tyr Asn Asp Ile Gln Ile Lys
                85                  90                  95

Ile Lys Ile Asn Gln Asn Glu Lys Glu Ile Lys Lys Val Leu Pro Gln
            100                 105                 110

Leu Tyr Ile Pro Lys Asn Glu Gln Glu Tyr Ile Gln Ile Tyr Lys Asn
        115                 120                 125

Glu Leu Lys Asp Arg Ile Lys Glu Thr Gln Thr Lys Ile Asn Leu Phe
130                 135                 140

Lys Gln Ile Leu Glu Leu Lys Lys Glu His Tyr Ile Thr Asn Lys
145                 150                 155                 160

His Thr Tyr Leu Asn Phe Thr His Lys Thr Ile Gln Gln Ile Leu Gln
                165                 170                 175

Gln Gln Tyr Lys Asn Asn Thr Gln Glu Lys Asn Thr Leu Ala Gln Phe
            180                 185                 190

Leu Tyr Asn Ala Asp Ile Lys Lys Tyr Ile Asp Glu Leu Ile Pro Ile
        195                 200                 205

Thr Gln Gln Ile Gln Thr Lys Met Tyr Thr Thr Asn Asn Ile Glu His
210                 215                 220

Ile Lys Gln Ile Leu Ile Asn Tyr Ile Gln Glu Cys Lys Pro Ile Gln
225                 230                 235                 240

Asn Ile Ser Glu His Thr Ile Tyr Thr Leu Tyr Gln Glu Ile Lys Thr
                245                 250                 255

Asn Leu Glu Asn Ile Glu Gln Lys Ile Met Gln Asn Ile Gln Gln Thr
            260                 265                 270

Thr Asn Arg Leu Lys Ile Asn Ile Lys Lys Ile Phe Asp Gln Ile Asn
        275                 280                 285

Gln Lys Tyr Asp Asp Leu Thr Lys Asn Ile Asn Gln Met Asn Asp
290                 295                 300

<210> SEQ ID NO 41
<211> LENGTH: 483
<212> TYPE: PRT
<213> ORGANISM: Plasmodium falciparum

<400> SEQUENCE: 41

```
Ile Asn Glu Ile Lys Ser Lys Met Asp Asn Ile Asn Glu Lys Leu Lys
1               5                   10                  15

His Ile Thr Asp Phe Ile Asp Lys Asn Val Asn Tyr Ile Tyr Glu Asn
            20                  25                  30

His Ser Thr Gln Asp Ile Asn Ile Met Leu Asn Asn Thr Ile Ser Glu
        35                  40                  45

Tyr Asn Lys Leu Glu Phe Ile Asn Ser Asp Ile Phe Asp Asn Ile Ser
50                  55                  60

Lys Lys Leu Lys Glu Leu Gln Asp Leu Val Thr Leu Lys Glu Ser
65                  70                  75                  80

Leu Met Lys Met Asn His Asn Val Leu Lys Met Asp Pro Leu Lys Ser
                85                  90                  95

Leu Asn Gln Val Leu Glu Lys Tyr Glu Leu Lys Lys Asn Ile Asn
            100                 105                 110

Glu Tyr Ser Lys Glu Gly Asn Lys Leu Tyr Asp Phe Lys Lys Gln Met
        115                 120                 125

Glu Ser Arg Leu Asn Ala Phe Ile Thr Asn Leu Asn Asn Asn Asp Glu
130                 135                 140

Thr Leu Val Asp Gly Lys Asn Ile Tyr Asp Gln Phe Val Glu Tyr Lys
145                 150                 155                 160

Glu Gln Leu Leu Ile Lys Lys Arg Ile Ile Asn Asn Glu Ile Val
                165                 170                 175

Ile Ile Asn Asp Glu Val Lys Lys Ile Lys Asp Glu Leu Lys Ser Tyr
            180                 185                 190

Asn Ile Leu Ser Tyr Lys Leu Glu Asn Asp Thr Ser His Asp Val Val
        195                 200                 205

Asn Ser Val Glu Asn Thr Pro Ser Ser Asp Val Ala Thr Ala Val Ser
210                 215                 220

Asn Ser Ser Ser Ile Leu Ser Thr Tyr Asn Ser Thr Glu Leu Asn Lys
225                 230                 235                 240

Leu Arg Asn Phe Phe Ser Glu Lys Asp Asp Glu Leu Asn Val Glu Ser
                245                 250                 255

Lys Val Lys Gln Asp Glu Asn Ile Phe Ile Glu Lys Asn Lys Ile Phe
            260                 265                 270

Asp Asp Ile Ile Lys Asp Ile Glu Leu Tyr Asn Lys Lys Thr Asn Ala
        275                 280                 285

Ile Lys Asn Leu Asn Asn Ala Ile Asn Gly Ser Met Asn Asn Leu Ser
290                 295                 300

Leu Ile Asp Ser Val Met Lys Asn Lys Gly Asp Ile Ile Asn Arg Leu
305                 310                 315                 320

Ser Gln Arg Ser Tyr Leu Ile Gln Thr Asp Asn Phe Ile Asp Ile Tyr
                325                 330                 335

Glu Lys Ile Phe Leu Lys Asp Asn Leu Asn Lys Gly Leu Glu Glu Ile
            340                 345                 350

Glu Asn Arg Leu Ser Asn Thr Tyr Met Asn Glu Leu Lys Ile Glu Ala
        355                 360                 365

Glu Lys Gln Asn Glu Lys Tyr Lys Lys Leu Lys Glu Asn Ile Asn Thr
370                 375                 380

Tyr Asp Asp Thr Phe Leu Glu Lys Leu Ile Gly Asp Asn Tyr Glu Trp
385                 390                 395                 400

Glu Val Leu Lys Ile Glu Leu Asn Gly Leu Asn Val Asn Tyr Asn Ile
                405                 410                 415
```

```
Leu Gln Ala Asn Ile Asp Thr Leu Ile Ile Lys Pro Tyr Ile Asp His
                420                 425                 430

Ile Asp His Ile Ile Ser Leu Ile Glu Ser Leu Lys His Asn Ile Glu
            435                 440                 445

Asn Lys Ile Lys Lys Val Ile Pro Asn Leu Glu Arg Leu Lys Asp Phe
450                 455                 460

Ile Gln Thr Lys Phe Asn Thr Asn Asp Ile Lys Leu Asp His Asn Asn
465                 470                 475                 480

Leu Ile Thr

<210> SEQ ID NO 42
<211> LENGTH: 303
<212> TYPE: PRT
<213> ORGANISM: Plasmodium vivax

<400> SEQUENCE: 42

Ile Asn Asp Leu Gln Asp Leu Ile Asp Gln Met Lys Glu Tyr Lys Asp
1               5                   10                  15

Glu Ile Val Asn Asn Ser Glu Phe Ile Ser Asn Arg Tyr Lys Asn Ile
                20                  25                  30

Tyr Glu Asn Leu Lys Glu Thr Tyr Glu Thr Glu Leu Asn Asp Ile Gly
            35                  40                  45

Lys Leu Glu Asn Asp Thr Ser Lys Val Asn Phe Tyr Leu Met Gln Ile
50                  55                  60

Arg Lys Ile Asn Thr Glu Lys Thr Lys Ile Asp Glu Ser Leu Gln Thr
65                  70                  75                  80

Val Glu Lys Phe Tyr Lys Glu Ile Leu Asp Ser Lys Glu Lys Ile Tyr
                85                  90                  95

Glu Leu Lys Ile Glu Phe Glu Lys Ser Val Thr Glu Ile Asn Arg Leu
            100                 105                 110

Gln Asp Gly Glu Ser Ala Arg Asp Leu His Glu Glu Gln Ile Lys Glu
        115                 120                 125

Ile Leu Asp Lys Met Ala Lys Lys Val His Tyr Leu Lys Glu Leu Leu
130                 135                 140

Ser Leu Lys Gly Lys Ser Ser Val Tyr Phe Thr Glu Met Asn Glu Leu
145                 150                 155                 160

Leu Asn Thr Ala Ser Tyr Asp Asn Met Glu Gly Phe Ser Ala Lys Lys
                165                 170                 175

Glu Lys Ala Asp Asn Asp Ile Asn Ala Leu Tyr Asn Ser Val Tyr Arg
            180                 185                 190

Glu Asp Ile Asn Ala Leu Ile Glu Glu Val Lys Phe Val Thr Glu
        195                 200                 205

Asn Lys Glu Ser Thr Leu Glu Met Leu Lys Asp Glu Glu Met Glu Glu
210                 215                 220

Lys Leu Gln Asp Ala Lys Glu Thr Phe Ala Lys Leu Asn Phe Val Ser
225                 230                 235                 240

Asp Asp Lys Leu Thr Asp Val Tyr Thr Lys Met Ser Ala Glu Val Thr
                245                 250                 255

Asn Ala Glu Gly Ile Lys Lys Gly Ile Ala Gln Lys Gln Phe Glu Asn
            260                 265                 270

Val His Lys Lys Met Lys Glu Phe Ser Asp Ala Phe Ser Thr Lys Phe
        275                 280                 285

Glu Ala Leu Gln Asn Ser Met Gln Gln Tyr Asn Gln Glu Gly Asp
290                 295                 300
```

```
<210> SEQ ID NO 43
<211> LENGTH: 408
<212> TYPE: PRT
<213> ORGANISM: Plasmodium vivax

<400> SEQUENCE: 43

Leu Gln Lys Val Glu Ser Asp Ile Tyr Arg Val Glu Leu Lys Thr Leu
1               5                   10                  15

Phe Tyr Val Ala Ala Lys His Tyr Ala Asp Phe Lys Phe Ser Leu Glu
            20                  25                  30

His Leu Lys Met Phe Glu Asn Leu Ser Lys Ser Lys Glu Lys Met Leu
        35                  40                  45

Tyr Ser Thr Phe Glu Lys Leu Glu Gly Asp Leu Leu Asn Lys Ile Asn
    50                  55                  60

Thr Leu Met Gly Ser Glu Gln Ser Thr Ser Asp Leu Thr Ser Ile Ile
65                  70                  75                  80

Ala Asp Ser Glu Lys Ile Ile Lys Ser Ala Glu Ser Leu Ile Asn Ser
                85                  90                  95

Ser Ser Glu Glu Ile Ala Lys Tyr Ala Leu Asp Ser Asn Glu Lys Ile
            100                 105                 110

Asn Glu Ile Lys Lys Asn Tyr Asp Gln Asn Ile Leu Lys Val Arg Glu
        115                 120                 125

Phe Ile Asn Lys Ser Asn Gly Leu Ile Thr Ser Val Lys Gly Thr Ser
    130                 135                 140

Gln Leu Ser Glu Ser Asp Lys Gln Gln Ile Glu Thr Lys Ile Glu Glu
145                 150                 155                 160

Ile Lys Lys Lys Lys Lys Asp Ile Leu Glu Arg Gly Lys Glu Phe Ile
                165                 170                 175

Asn Ile Met Asn Glu Ile Lys Lys Lys Lys Ser Asn Ser Ser Asn
            180                 185                 190

Ser Ser Thr Asn Ser Lys Glu Phe Thr Asp Lys Leu Lys Glu Leu Glu
        195                 200                 205

Thr Glu Phe Glu Gly Leu Asn Lys Thr Val Lys Gly Tyr Leu Gln Glu
    210                 215                 220

Ile Glu Asp Ile Lys Val Lys Glu Asn Glu Asp Arg Ser Leu Lys Asn
225                 230                 235                 240

Gln Ile Glu Gln His Leu Lys Tyr Thr Ser Asp Asn Arg Asp Asn Val
                245                 250                 255

Lys Thr Leu Ile Ser Lys Asn Asp Glu Ile Gln Lys Tyr Ile Glu Lys
            260                 265                 270

Ile Glu Lys Leu Ile Asn Asp Ala Pro Ser Gly Lys Asp Lys Phe Thr
        275                 280                 285

Thr Glu Lys Thr Asn Leu Gln Asn Lys Val Lys Lys Ile Ile Asp Glu
    290                 295                 300

Phe His Lys Glu Asp Leu Gln Leu Leu Leu Asn Ser Leu Ser Lys Phe
305                 310                 315                 320

Tyr Glu Glu His Gln Lys Leu Tyr Asn Glu Ala Ser Thr Ile Glu Lys
                325                 330                 335

Ile Lys Asp Leu His Gln Lys Thr Lys Glu Glu Tyr Glu Lys Leu Glu
            340                 345                 350

Lys Met Lys Phe Ser Asn Phe Gly Gln Ile Leu Asp Lys Leu Asn Thr
        355                 360                 365

Glu Leu Asp Asn Leu Lys Thr Leu Glu Lys Asn Ile Val Glu Glu Gln
    370                 375                 380
```

```
-continued

Thr Asn Tyr Ile Asn Lys Val Met Ser Asp Ser Leu Thr Asn Leu Thr
385                 390                 395                 400

Ala Glu Val Asp Asn Leu Arg Ser
                405
```

BINDING DOMAIN OF *PLASMODIUM* RETICULOCYTE BINDING PROTEINS

FIELD OF THE INVENTION

The present invention provides isolated polynucleotides, polypeptides, antibodies and/or vaccines for the prevention and/or treatment of malaria caused by *Plasmodium* merozoites, in particular *Plasmodium falciparum* and/or *Plasmodium vivax*.

BACKGROUND OF THE INVENTION

Malaria is caused by parasites of the genus *Plasmodium* and causes an estimated 300-500 million clinical cases and 1-3 million deaths annually (Snow et al, 2005). In addition to morbidity and mortality the economic burden due to malaria is immense, with loss of up to 1-2% of GDP per year estimated for some countries where malaria is endemic.

An essential step in the life cycle of malaria parasites is the invasion of host erythrocytes by merozoites. The invasion process is characterized by a multitude of specific, but relatively poorly understood, interactions between protein ligands expressed by the merozoite and receptors on the erythrocyte surface (Cowman A F and Crabb B S, 2006). Several molecules implicated in the invasion process have been identified in the apical organelles (rhoptry, micronemes, and dense granules) of the merozoite. At least two gene families the Reticulocyte Binding Protein homologues (RH) and the family of erythrocyte binding proteins/ligands (EBL) have been shown to mediate specific interactions with host cell receptors thereby defining host cell specificity and are thought to play an important role in parasite virulence and possibly immune evasion (Gaur et al., 2004; Iyer et al., 2007).

In the human parasite *Plasmodium falciparum* two gene families termed Erythrocyte Binding Like Proteins (or EBL) and the Reticulocyte Binding Protein Homologues (RBPH) have been shown to play a crucial role in the selection of suitable host cells. Both EBL and RBPH are thought to directly interact with specific receptors on the red blood cell surface. In the case of EBL the region within the protein that directly mediates binding has been identified. This region called Duffy Binding Like Domain (DBL) is characterized by a number of conserved cysteine residues and is conserved in all members of this gene family. In contrast no binding region of any RBPH member has so far been identified. Considering the large size of these proteins (up to 300 kDa) it is crucial to dissect the protein into smaller functional domains.

Numerous studies have indicated that malarial merozoites can invade erythrocytes through several invasion pathways. This ability is dependent on the repertoire of parasite ligands expressed at the surface of the parasite and variations of receptors at the erythrocyte surface. The various alternative invasion pathways are classified according to the nature of the erythrocyte receptors involved in invasion, which in turn are operationally defined by the enzymatic treatments upon erythrocytes which disrupt binding. *P. falciparum* EBA-175, one of the EBL members, is the best characterized receptor and recognizes sialic acid components on Glycophorin A (Sim B K L et al, 1994). Other EBLs have been shown to interact with a Glycophorin B and C as well as the Duffy blood group antigen.

In *P. falciparum* five RH members PfRH1, PfRH2a & 2b, PfRH3, and PfRH4 have been identified (Cowman A F and Crabb B S, 2006). Recognition of erythrocytes by PfRH1 is sialic acid dependent and trypsin resistant (Rayner J C et al, 2001), whereas that of PfRH2b is sialic acid independent and trypsin resistant (Duraisingh et al., 2003), and that of PfRH4 is sialic acid independent and trypsin resistant (Stubbs et al, 2005). While all these studies indicate that RH recognizes a specific receptor on the erythrocyte surface, only in the case of PfRH1 has direct binding to red blood cells been demonstrated.

How binding of EBL or RH to specific erythrocyte receptors ultimately leads to merozoite invasion is an important question that requires the parasite ligand to be dissected into functional domains.

SUMMARY OF THE INVENTION

The present invention addresses the problems above and provides at least one *Plasmodium* reticulocyte Binding Protein homologue (RH) fragments that is involved in the binding to and/or invasion of the erythrocytes by the parasite. The present invention therefore provides effective preventive and/or therapeutic measures against *Plasmodium* invasion.

Accordingly, the present invention provides at least one isolated polypeptide, wherein the polypeptide is a *Plasmodium* Reticulocyte Binding Protein homologue (RH) fragment, comprising or substantially comprising at least one amino acid sequence selected from SEQ ID NO: 2, SEQ ID NO: 4, SEQ ID NO: 6 and SEQ ID NO: 8, a homologue or a portion thereof. In particular the isolated polypeptide comprises at least one amino acid sequence selected from SEQ ID NO: 4, SEQ ID NO: 6 and SEQ ID NO: 8, a homologue and/or a portion thereof. More in particular the at least one polypeptide comprises at least the amino acid of SEQ ID NO: 8, a homologue and/or a portion thereof. The isolated polypeptide sequence may be less than 700 amino acids, in particular less than 550 amino acids. The isolated polypeptide sequence may be selected from PfRH1, PvRBP1 and/or a homologue thereof.

According to another aspect, the invention provides an isolated polypeptide comprising or substantially comprising at least one amino acid sequence selected from SEQ ID NO: 2, SEQ ID NO: 4, SEQ ID NO: 6 and SEQ ID NO: 8, a homologue or a portion thereof, wherein the polypeptide comprises less than 700. In particular, the polypeptide comprises less than 550 amino acids. More in particular, the polypeptide according to the invention consists of at least one amino acid sequence selected from SEQ ID NO: 2, SEQ ID NO: 4, SEQ ID NO: 6 and SEQ ID NO: 8, a homologue or a portion thereof.

The invention also provides an isolated polynucleotide encoding a polypeptide comprising, substantially comprising or consisting of, at least one nucleic acid sequence selected from SEQ ID NO: 1, SEQ ID NO: 3, SEQ ID NO: 5 and SEQ ID NO: 7, a homologue and/or a portion thereof. In particular, the polynucleotide may comprise, substantially comprise or consist of at least one nucleic acid sequence selected from SEQ ID NO: 3, SEQ ID NO: 5 and SEQ ID NO: 7, a homologue and/or a portion thereof. More in particular the at least one nucleic acid sequence may be SEQ ID NO: 7, a homologue and/or a portion thereof. There is also provided a vector comprising the isolated polynucleotide. Further, there is provided at least one host cell comprising vector or the polynucleotide according to the invention.

According to another aspect, the invention provides a method of producing the polypeptide according comprising the steps of:
 (a) culturing the cell comprising the vector, under conditions suitable for expression of the polypeptide; and
 (b) recovering the polypeptide so expressed.

The recovered polypeptide may comprise at least one of the amino acid sequence selected from SEQ ID NO: 2, SEQ ID NO: 4, SEQ ID NO: 6 and SEQ ID NO: 8, a homologue and/or a portion thereof. In particular, the polypeptide may comprise at least the amino acid sequence of SEQ ID NO: 8, a homologue and/or a portion thereof.

According to yet another aspect of the invention, there is provided an isolated antibody, wherein the antibody specifically binds to a polypeptide comprising, substantially comprising or consisting of at least one amino acid sequence selected from SEQ ID NO: 2, SEQ ID NO: 4, SEQ ID NO: 6 and SEQ ID NO: 8, a homologue and/or a portion thereof. In particular, the antibody may specifically bind to a polypeptide comprising, substantially comprising or consisting of the amino acid sequence of SEQ ID NO: 2 and SEQ ID NO: 8 a homologue and/or a portion thereof. The antibody may be monoclonal, polyclonal, chimeric, humanised, single chain, Fab, Fab', F(ab)' fragments and/or F(v) portions of the whole antibody.

According to a further aspect, the invention provides a pharmaceutical composition for reducing and/or inhibiting the binding to and/or invasion of *Plasmodium* into erythrocytes, comprising
- (a) at least one antibody and/or portion thereof, capable of binding to at least one amino acid sequence selected from SEQ ID NO: 2, SEQ ID NO: 4, SEQ ID NO: 6 and SEQ ID NO: 8, a homologue or a portion thereof; and/or
- (b) at least one polypeptide comprising, substantially comprising or consisting of at least one amino acid sequence selected from SEQ ID NO:2, SEQ ID NO: 4, SEQ ID NO: 6 and SEQ ID NO: 8, a homologue and/or a portion thereof; and/or
- (c) at least one nucleic acid molecule hybridizing and/or complementary to any part of the polynucleotide comprising, substantially comprising or consisting of at least one nucleic acid sequence selected from SEQ ID NO: 1, SEQ ID NO: 3, SEQ ID NO: 5 and SEQ ID NO: 7, a homologue and/or a portion thereof, optionally in the presence of at least one pharmaceutically acceptable excipient, diluent, carrier, adjuvant and/or a combination thereof.

There is also provided a method of treating and/or preventing malaria comprising administering to a subject in need a composition comprising
- (a) at least one antibody and/or portion thereof, capable of binding to at least one amino acid sequence selected from SEQ ID NO: 2, SEQ ID NO: 4, SEQ ID NO: 6 and SEQ ID NO: 8, a homologue or a portion thereof; and/or
- (b) at least one polypeptide comprising, substantially comprising or consisting of at least one amino acid sequence selected from SEQ ID NO:2, SEQ ID NO: 4, SEQ ID NO: 6 and SEQ ID NO: 8, a homologue and/or a portion thereof; and/or
- (c) at least one nucleic acid molecule capable of hybridizing and/or complementary to any part of the polynucleotide comprising, substantially comprising or consisting of at least one nucleic acid sequence selected from SEQ ID NO: 1, SEQ ID NO: 3, SEQ ID NO: 5 or SEQ ID NO: 7, a homologue and/or a portion thereof.

The method may comprise reducing and/or inhibiting the binding to and/or invasion of *Plasmodium* into erythrocytes, wherein the subject may be a mammal. In particular the subject may be a human.

According to yet another aspect of the invention there is provided a use of
- (a) at least one antibody and/or portion thereof, capable of binding to at least one amino acid sequence selected from SEQ ID NO: 2, SEQ ID NO: 4, SEQ ID NO: 6 and SEQ ID NO: 8, a homologue or a portion thereof; and/or
- (b) at least one polypeptide comprising, substantially comprising or consisting of at least one amino acid sequence selected from SEQ ID NO:2, SEQ ID NO: 4, SEQ ID NO: 6 and SEQ ID NO: 8, a homologue and/or a portion thereof; and/or
- (c) at least one nucleic acid molecule hybridizing and/or complementary to any part of the polynucleotide comprising, substantially comprising or consisting of at least one nucleic acid sequence selected from SEQ ID NO: 1, SEQ ID NO: 3, SEQ ID NO: 5 and SEQ ID NO: 7, a homologue and/or a portion thereof, in preparation of a medicament for use in therapy. In particular, the medicament may be for treating and/or preventing malaria. More in particular, the medicament may be for reducing and/or inhibiting the binding to and/or invasion of *Plasmodium* into erythrocytes.

There is also provided at least one polypeptide, at least one polynucleotide and/or at least one antibody according to the invention for use in therapy. In particular, the polypeptide, polynucleotide and/or antibody may be for treating and/or preventing malaria, and more in particular, for reducing and/or inhibiting the binding to and/or invasion of *Plasmodium* into erythrocytes.

According to a further aspect, the invention provides a method of diagnosis and/or prognosis of malaria in a subject, comprising:
- (a) providing at least one sample from a subject;
- (b) detecting the presence of at least one polynucleotide comprising, substantially comprising or consisting of at least one nucleic acid sequence selected from SEQ ID NO: 1, SEQ ID NO: 3, SEQ ID NO: 5 and SEQ ID NO: 7, a homologue and/or a portion thereof; and/or
- (c) detecting the presence of at least one polypeptide comprising, substantially comprising or consisting of the amino acid sequence of SEQ ID NO: 2, SEQ ID NO: 4, SEQ ID NO: 6 or SEQ ID NO: 8, a homologue and/or a portion thereof;

wherein the presence of the polynucleotide and/or the polypeptide is indicative of presence of *Plasmodium* in the subject. The step (c) may be in the presence of at least one antibody capable of binding to at least one polypeptide comprising, substantially comprising or consisting of the amino acid sequence selected from SEQ ID NO: 2, SEQ ID NO: 4, SEQ ID NO: 6 and SEQ ID NO: 8, a homologue and/or a portion thereof. The at least one polypeptide may comprise, substantially comprise or consists of the amino acid sequence of SEQ ID NO: 8, a homologue and/or a portion thereof. The subject may be a mammal, in particular a human.

According to yet another aspect the invention provides a diagnostic and/or prognostic kit for the diagnosis and/or prognosis of malaria in a subject comprising
- (a) at least one antibody and/or portion thereof, capable of binding to at least one amino acid sequence selected from SEQ ID NO: 2, SEQ ID NO: 4, SEQ ID NO: 6 and SEQ ID NO: 8, a homologue or a portion thereof; and/or
- (b) at least one nucleic acid molecule capable of hybridizing and/or complementary to any part of the polynucleotide comprising, substantially comprising or consisting of at least one of the sequences selected from SEQ ID NO: 1, SEQ ID NO: 3, SEQ ID NO: 5 or SEQ ID NO: 7, a homologue and/or a portion thereof, wherein the subject may be a mammal, in particular the subject may be a human.

According to another aspect of the present invention there is provided a method of inducing a protective immune response to *Plasmodium* merozoites in a subject comprising administering to the subject an immunologically effective amount of at least one polypeptide comprising, substantially comprising or consisting of at least one amino acid sequence selected from SEQ ID NO: 2, SEQ ID NO: 4, SEQ ID NO: 6 and SEQ ID NO: 8, a homologue and/or a portion thereof. Optionally, the polypeptide may be in combination with at least one pharmaceutically acceptable excipient, carrier, adjuvant and/or additive. There is also provided a pharmaceutical composition comprising the at least one polypeptide in combination with at least one pharmaceutically acceptable excipient, carrier, diluent, adjuvant and/or additive. The at least one polypeptide may comprise, substantially comprise or consist of the amino acid sequence of SEQ ID NO: 8, a homologue and/or a portion thereof.

According to yet another aspect of the invention, there is provided a recombinant DNA vaccine comprising an expression vector for expression of a polynucleotide, the polynucleotide comprising, substantially comprising or consisting of at least one nucleic acid sequence selected from SEQ ID NO: 1, SEQ ID NO: 3, SEQ ID NO: 5 and SEQ ID NO: 7, a homologue and/or a portion thereof, optionally in the presence of at least one pharmaceutically acceptable excipient, carrier, adjuvant, diluent and/or additive. The at least one polynucleotide may comprise, substantially comprise or consists of the nucleic acid sequence of SEQ ID NO: 7, a homologue and/or a portion thereof. The polynucleotide may encode for an immunogenic peptide, comprising, substantially comprising or consisting of at least one of the amino acid sequence selected from SEQ ID NO: 2, SEQ ID NO: 4, SEQ ID NO: 6 and SEQ ID NO: 8, a homologue and/or a portion thereof, wherein the at least one amino acid sequence comprises, substantially comprises or consists of the sequence of SEQ ID NO: 8, a homologue and/or a portion thereof. The recombinant vaccine may be for use in a mammal, in particular a human.

According to a further aspect the invention provides, a method of vaccinating a subject against malaria comprising administering to the subject in need an effective amount of a recombinant DNA vaccine capable of expressing an immunogenic peptide comprising, substantially comprising or consisting of at least one amino acid sequence selected from SEQ ID NO: 2, SEQ ID NO: 4, SEQ ID NO: 6 and SEQ ID NO: 8, a homologue and/or a portion thereof after administration of the vaccine to a subject. The at least one amino acid sequence may comprise, substantially comprise or consist of the sequence of SEQ ID NO: 8, a homologue and/or a portion thereof. The subject may be a mammal, in particular a human.

BRIEF DESCRIPTION OF THE FIGURES

FIG. 5 represents bioinformatic analysis of the minimal binding region RII-3 of PfRH1. (A) Alignment and secondary structural prediction of putative erythrocyte binding region of *P. falciparum* RHs family members, PfRH1-RII-3 SEQ ID NO:8), PfRH2A (SEQ ID NO:38) and PfRH4 (SEQ ID NO:40). Red or dark grey with "*" underneath indicates identical residues, blue or black with ":" underneath indicates conserved residues and green or light grey with "." indicates semi-conserved residues. Secondary structure is shown above the sequence alignment with α-helix in purple or dark grey and β-sheet shown as arrow in purple or dark grey. Dashed lines indicate regions not observed in the predicted secondary structure. (B) Approximate locations of predicated erythrocyte binding regions of different *plasmodium* species, *P. falciparum*—PfRH1-RII-3; *P. yoelii*—Py235; *P. vivax*—PvRBP1 and PvRBP2. The homologous regions of PfRH1-RII-3 erythrocyte binding region are indicated as light grey boxes. (C) Results of the coiled coils prediction methods for the RII-3 minimal binding protein. The calculation was done using three different window sizes of 14, 21 and 28 amino-acids respectively.

FIG. 6 represents the predicted binding regions of the RH orthologues in *P. falciparum* and *P. vivax*. Binding regions were identified using PfRH1-RII-3 (SEQ ID NO: 8) vs predicted binding regions of other RH members (using ClustalW), namely the *P. falciparum* homologues PfRH2A (SEQ ID NO: 38), PfRH2B (SEQ ID NO: 39), PfRH4 (SEQ ID NO: 40), PfRH3 (SEQ ID NO: 41) and the *P. vivax* homologues, PvRBP-1 (SEQ ID NO: 42), PvRBP-2 (SEQ ID NO: 43).

FIG. 7 (A) Western analysis of PfRH1 expression on the merozoite extracts supernatant probed with αrRII-3 (Lane 1), αrtRVIII (Lane 2), Pre-immune serum (Lane 3) and normal RBC lysate supernatant?? (Lane 4). The expected protein of about 240 kDa was detected by both antisera (arrow). Size markers are shown in kilodaltons. (B) IFA analysis of smear of free merozoites reacted with αrRII-3, (C) merozoites reacted with αrtRVIII and (D) merozoites reacted with pre-immune serum. The parasites nuclei stained with DAPI (panel 1) are shown in first column; for the image in the second column, secondary antibody used was red AlexaFlour 594 goat anti-mouse IgG (H+L) (panel 2); the merge column shows the overlap between the first and second columns (panel 3). (E) represents invasion inhibition assay represented as percentage (%) inhibition of the W2mef strain in the presence of antibodies, RII-3 or tRVIII, or preimmune serum at various dilutions.

BRIEF DESCRIPTION OF THE SEQUENCES

Figure 1:
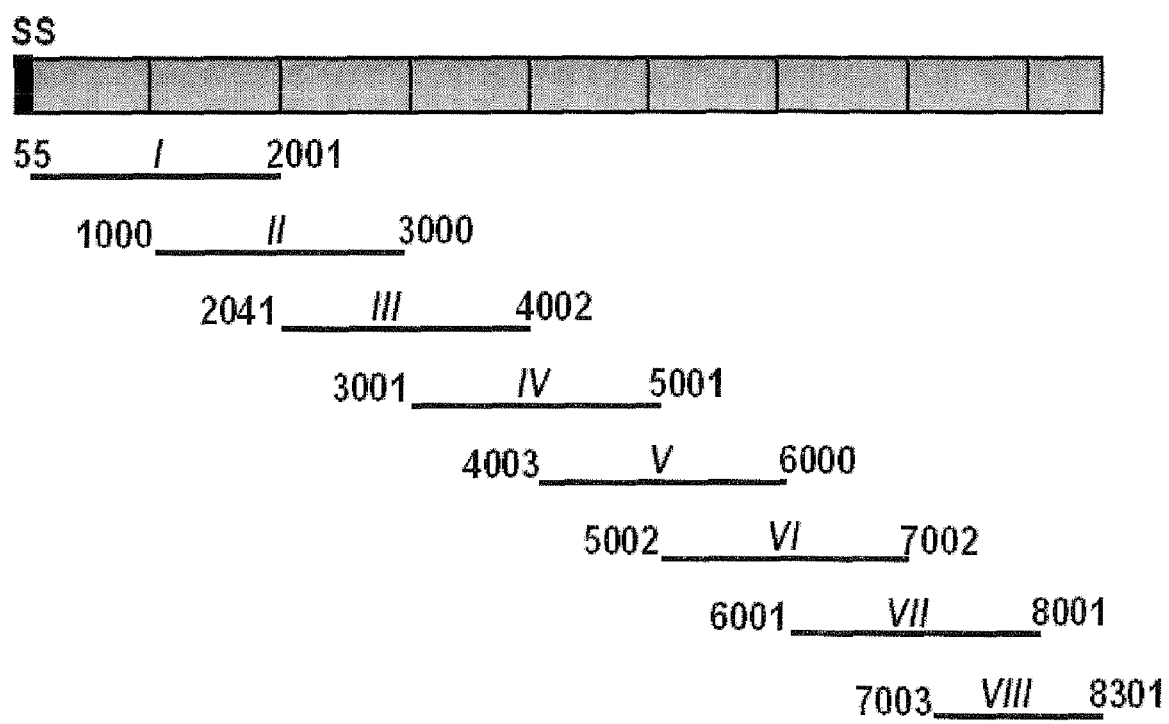
FIG. 1 represents chimeric constructs for the expression of different regions of genomic sequence from PfRH1 with intro spliced out in 3D7 on COS7 cells. *P. falciparum* 3D7 clone with intron spliced out (Genbank accession no: AF533700). Sequence includes signal sequence (SS, black) and Exon2 (grey) encoding a large extracellular domain. Figure represents the extracellular domain divided into eight regions (From/to VIII). Each region (black line with bp no.) is approximately 2 Kb with 1 Kb overlap between 2 regions except VIII, which is 1.3 Kb.

SEQ ID NO: 1 refers to the polynucleotide sequence of region II (RII) fragment, encoding the binding domain polypeptide, of *P. falciparum* PfRH1:

AAAGATGTAATAAATAATAAGATAGATATATATAAAACAATAAGTTCTT
TTATATCTACTCAGAAACAATTATATTATTTTGAATATATATATATAAT
GAATAAAAATACATTAAACCTACTTTCATATAATATACAAAAAACAGAT
ATAAATTCTAGTAGTAAATACACATATACAAAATCTCATTTTTTAAAAG
ATAATCATATATTGTTATCTAAATATTATACTGCCAAATTTATTGATAT
CCTAAATAAAACATATTATTATAATTTATATAAAAATAAAATTCTTTTA
TTCAATAAATATATTATAAAGCTTAGAAACGATTTAAAAGAATATGCAT
TTAAATCTATACAATTTATTCAAGATAAAATCAAAAAACATAAGATGA
ATTATCCATAGAAAATATATTACAAGAAGTTAATAATATATATATAAAA
TATGATACTTCGATAAATGAAATATCTAAATATAACAATTTAATTATTA
ATACTGATTTACAAATAGTACAACAAAAACTTTTAGAAATCAAACAAAA
AAAAAATGATATTACACACAAAGTACAACTTATAAATCATATATATAAA
AATATACATGATGAAATATTAAACAAAAAAATAATGAAATAACAAAGA
TTATTATAAATAATATAAAAGATCATAAAAAAGATTTACAAGATCTCTT
ACTATTTATACAACAAATCAAACAATATAATATATTAACAGATCATAAA
ATTACACAATGTAATAATTATTATAAGGAAATCATAAAAATGAAAGAAG
ATATAAATCATATTCATATATATATACAACCAATTCTAAATAATTTACA
CACATTAAAACAAGTACAAAATAATAAAATCAAATATGAAGAGCACATC
AAACAAATATTACAAAAAATTTATGATAAAAAGGAATCTTTAAAAAAAA
TTATTCTCTTAAAAGATGAAGCACAATTAGACATTACCCTCCTCGATGA
CTTAATACAAAAGCAAACAAAAAAACAAACACAAACACAAACACAAACA
CAAAAACAAACACTAATACAAAATAATGAGACGATTCAACTTATTTCTG
GACAAGAAGATAAACATGAATCCAATCCATTTAATCATATACAAACCTA
TATTCAACAAAAAGATACACAAAATAAAAACATCCAAAATCTTCTTAAA
TCCTTGTATAATGGAAATATTAACACATTCATAGACACAATTTCTAAAT
ATATATTAAAACAAAAGATATAGAATTAACACAACACGTTTATACAGA
CGAAAAAATTAATGATTATCTTGAAGAAATAAAAAATGAACAAAACAAA
ATAGATAAGACCATCGACGATATAAAAATACAAGAAACATTAAAACAAA
TAACTCATATTGTTAACAATATAAAAACCATCAAAAGGATTTGCTCAA
AGAATTTATTCAACATTTAATAAAATATATGAACGAAAGATATCAGAAT
ATGCAACAGGGTTATAATAATTTAACAAATTATATTAATCAATATGAAG

AAGAAAATAATAATATGAAACAATATATTACTACCATACGAAATATCCA
AAAAATATATTATGATAATATATATGCTAAGGAAAAGGAAATTCGCTCG
GGACAATATTATAAGGATTTTATCACATCAAGGAAAAATATTTATAATA
TAAGGGAAAATATATCCAAAAATGTAGATATGATAAAAAATGAAGAAAA
GAAGAAAATACAGAATTGTGTAGATAAATATAATTCTATAAAACAATAT
GTAAAAATGCTTAAAAATGGAGACACACAAGATGAAAATAATAATAATA
ATAATGATATATACGACAAGTTAATTGTCCCCCTTGATTCAATAAAACA
AAATATCGATAAATACAACACAGAACATAATTTTATAACATTTACAAAT
AAAATAAATACACATAATAAGAAGAACCAAGAAATGATGGAAGAATTCA
TATATGCATATAAAAGGTTAAAAATTTTAAAAATATTAAAT

SEQ ID NO: 2 refer to the polypeptide sequence of region II (RII) fragment of *P. falciparum* PfRH1.

KDVINNKIDIYKTISSFISTQKQLYYFEYIYIMNKNTLNLLSYNIQKTD
INSSSKYTYTKSHFLKDNHILLSKYYTAKFIDILNKTYYYNLYKNKILL
FNKYIIKLRNDLKEYAFKSIQFIQDKIKKHKDELSIENILQEVNNIYIK
YDTSINEISKYNNLIINTDLQIVQQKLLEIKQKKNDITHKVQLINHIYK
NIHDEILNKKNNEITKIIINNIKDHKKDLQDLELFIQQIKQYNILTDHK
ITQCNNYYKEIIKMKEDINHIHIYIQPIENNEHTLKQVQNNKIKYEEHI
KQILQKIYDKKESLKKIILLKDEAQLDITLLDDLIQKQTKKQTQTQTQT
QKQTLIQNNETIQLISGQEDKHESNPFNHIQTYIQQKDTQNKNIQNLLK
SLYNGNINTFIDTISKYILKQKDIELTQHVYTDEKINDYLEEIKNEQNK
IDKTIEDIKIQETLKQITHIVNNIKTIKKDLLKEFIQHLIKYMNERYQN
MQQGYNNLTNYINQYEEENNNMKQYITTIRNIQKIYYDNIYAKEKEIRS
GQYYKDFITSRKNIYNIRENISKNVDMIKNEEKKKIQNCVDKYNSIKQY
VKMLKNGDTQDENNNNNNDIYDKLIVPLDSIKQNIDKYNTEHNFITFTN
KINTHNKKNQEMMEEFIYAYKRLKILKILN

SEQ ID NO: 3 refers to the polynucleotide sequence of a smaller PfRH1-RII (RII-1) fragment having deletion at the 3' end.

AAAGATGTAATAAATAATAAGATAGATATATATAAAACAATAAGTTCTT
TTATATCTACTCAGAAACAATTATATTATTTTGAATATATATATATAAT
GAATAAAAATACATTAAACCTACTTTCATATAATATACAAAAAACAGAT
ATAAATTCTAGTAGTAAATACACATATACAAAATCTCATTTTTTAAAAG
ATAATCATATATTGTTATCTAAATATTATACTGCCAAATTTATTGATAT
CCTAAATAAAACATATTATTATAATTTATATAAAAATAAAATTCTTTTA
TTCAATAAATATATTATAAAGCTTAGAAACGATTTAAAAGAATATGCAT
TTAAATCTATACAATTTATTCAAGATAAAATCAAAAAACATAAGATGA
ATTATCCATAGAAAATATATTACAAGAAGTTAATAATATATATATAAAA
TATGATACTTCGATAAATGAAATATCTAAATATAACAATTTAATTATTA
ATACTGATTTACAAATAGTACAACAAAAACTTTTAGAAATCAAACAAAA

-continued
```
AAAAAATGATATTACACACAAAGTACAACTTATAAATCATATATATAAA
AATATACATGATGAAATATTAAACAAAAAAAATAATGAAATAACAAAGA
TTATTATAAATAATATAAAAGATCATAAAAAAGATTTACAAGATCTCTT
ACTATTTATACAACAAATCAAACAATATAATATATTAACAGATCATAAA
ATTACACAATGTAATAATTATTATAAGGAAATCATAAAAATGAAAGAAG
ATATAAATCATATTCATATATATATACAACCAATTCTAAATAATTTACA
CACATTAAAACAAGTACAAAATAATAAAATCAAATATGAAGAGCACATC
AAACAAATATTACAAAAAATTTATGATAAAAAGGAATCTTTAAAAAAAA
TTATTCTCTTAAAAGATGAAGCACAATTAGACATTACCCTCCTCGATGA
CTTAATACAAAAGCAAACAAAAAAACAAACACAAACACAAACACAAACA
CAAAAACAAACACTAATACAAAATAATGAGACGATTCAACTTATTTCTG
GACAAGAAGATAAACATGAATCCAATCCATTTAATCATATACAAACCTA
TATTCAACAAAAAGATACACAAAATAAAAACATCCAAAATCTTCTTAAA
TCCTTGTATAATGGAAATATTAACACATTCATAGACACAATTTCTAAAT
ATATATTAAAACAAAAGATATAGAATTAACACAACACGTTTATACAGA
CGAAAAAATTAATGATTATCTTGAAGAAATAAAAAATGAACAAAACAAA
ATAGATAAGACCATCGACGATATAAAAATACAAGAAACATTAAAACAAA
TAACTCATATTGTTAACAATATAAAAACCATCAAAAAGGATTTGCTCAA
AGAATTTATTCAACATTTAATAAAATATATGAACGAAAGATATCAGAAT
ATGCAACAGGGTTATAATAATTTAACAAAT
```

SEQ ID NO: 4 refer to the polypeptide sequence of a smaller PfRH1-RII (RII-1) fragment having deletion at the 3' end.

```
KDVINNKIDIYKTISSFISTQKQLYYFEYIYIMNKNTLNLLSYNIQKTD
INSSSKYTYTKSHFLKDNHILLSKYYTAKFIDILNKTYYYNLYKNKILL
FNKYIIKLRNDLKEYAFKSIQFIQDKIKKHKDELSIENILQEVNNIYIK
YDTSINEISKYNNLIINTDLQIVQQKLLEIKQKKNDITHKVQLINHIYK
NIHDEILNKKNNEITKIIINNIKDHKKDLQDLLLFIQQIKQYNILTDFI
KITQCNNYYKEIIKMKEDINHIHIYIQPILNNLHTLKQVQNNKIKYEEH
IKQILQKIYDKKESLKKIILLKDEAQLDITLLDDLIQKQTKKQTQTQTQ
TQKQTLIQNNETIQLISGQEDKHESNPFNHIQTYIQQKDTQNKNIQNLL
KSLYNGNINTFIDTISKYILKQKDIELTQHVYTDEKINDYLEEIKNEQN
NIMKTIDDIKIQETLKQITHIVNNIKTIKKDLLKEFIQHLIKYMNERYQ
NMQQGYNNLTN
```

SEQ ID NO: 5 refers to the polynucleotide sequence of a smaller PfRH1-RII (RII-2) fragment having deletion at the 5' end.

```
TTACAAATAGTACAACAAAAACTTTTAGAAATCAAACAAAAAAAAATG
ATATTACACACAAAGTACAACTTATAAATCATATATATAAAAATATACA
TGATGAAATATTAAACAAAAAAATAATGAAATAACAAAGATTATTATA
AATAATATAAAAGATCATAAAAAAGATTTACAAGATCTCTTACTATTTA
TACAACAAATCAAACAATATAATATATTAACAGATCATAAAATTACACA
ATGTAATAATTATTATAAGGAAATCATAAAAATGAAAGAAGATATAAAT
CATATTCATATATATATACAACCAATTCTAAATAATTTACACACATTAA
AACAAGTACAAAATAATAAAATCAAATATGAAGAGCACATCAAACAAAT
ATTACAAAAAATTTATGATAAAAAGGAATCTTTAAAAAAAATTATTCTC
TTAAAAGATGAAGCACAATTAGACATTACCCTCCTCGATGACTTAATAC
AAAAGCAAACAAAAAAACAAACACAAACACAAACACAAACACAAAAACA
AACACTAATACAAAATAATGAGACGATTCAACTTATTTCTGGACAAGAA
GATAAACATGAATCCAATCCATTTAATCATATACAAACCTATATTCAAC
AAAAAGATACACAAAATAAAAACATCCAAAATCTTCTTAAATCCTTGTA
TAATGGAAATATTAACACATTCATAGACACAATTTCTAAATATATATTA
AAACAAAAGATATAGAATTAACACAACACGTTTATACAGACGAAAAAA
TTAATGATTATCTTGAAGAAATAAAAAATGAACAAAACAAAATAGATAA
GACCATCGACGATATAAAAATACAAGAAACATTAAAACAAATAACTCAT
ATTGTTAACAATATAAAAACCATCAAAAAGGATTTGCTCAAAGAATTTA
TTCAACATTTAATAAAATATATGAACGAAAGATATCAGAATATGCAACA
GGGTTATAATAATTTAACAATTATATTAATCAATATGAAGAAGAAAT
AATAATATGAAACAATATATTACTACCATACGAAATATCCAAAAATAT
ATTATGATAATATATGCTAAGGAAAAGGAAATTCGCTCGGGACAATA
TTATAAGGATTTTATCACATCAAGGAAAAATATTTATAATATAAGGGAA
AATATATCCAAAAATGTAGATATGATAAAAAATGAAGAAAAGAAGAAAA
TACAGAATTGTGTAGATAAATATAATTCTATAAAACAATATGTAAAAAT
GCTTAAAAATGGAGACACACAAGATGAAAATAATAATAATAATAATGAT
ATATACGACAAGTTAATTGTCCCCCTTGATTCAATAAAACAAAATATCG
ATAAATACAACACAGAACATAATTTTATAACATTTACAAATAAAATAAA
TACACATAATAAGAAGAACCAAGAAATGATGGAAGAATTCATATATGCA
TATAAAAGGTTAAAAATTTTAAAAAATATTAAAT
```

SEQ ID NO: 6 refer to the polypeptide sequence of a smaller PfRH1-RII (RII-2) fragment having deletion at the 5' end.

```
LQIVQQKLLEIKQKKNDITHKVQLINHIYKNIHDEILNKKNNEITKIII
NNIKDEKKDLQDLLLFIQQIKQYNILTDHKITQCNNYYKEIIKMKEDIN
EIHIYIQPILNNLETLKQVQNNKIKYEEHIKQILQKIYDKKESLKKIIL
LKDEAQLDIILLDDLIQKQTKKQTQTQTQTQKQTLIQNNETIQLISGQE
DKHESNPFNHIQTYIQQKDTQNKNIQNLLKSLYNGNINTFIDTISKYIL
KQKDIELTQHVYTDEKINDYLEEIKNEQNKIDKIIDDIKIQETLKQITH
IVNNIKTIKKDLLKEFIQHLIKYMNERYQNMQQGYNNLTNYINQYEEEN
NNMKQYITTIRNIQKIYYDNIYAKEKEIRSGQYYKDFITSRKNIYNIRE
NISKNVDMIKNEEKKKIQNCVDKYNSIKQYVKMLKNGDTQDENNNNNND
IYDKLIVPLDSIKQNIDKYNTEHNFITFTNKINTHNKKNQEMMEEFIYA
YKRLKILKILN
```

SEQ ID NO: 7 refer to the polynucleotide sequence of a smaller PfRH1-RII (RII-3) fragment having deletion at the 5' and the 3' end.

```
TTACAAATAGTACAACAAAAACTTTTAGAAATCAAACAAAAAAAAAATG
ATATTACACACAAAGTACAACTTATAAATCATATATATAAAAATATACA
TGATGAAATATTAAACAAAAAAAATAATGAAATAACAAAGATTATTATA
AATAATATAAAAGATCATAAAAAAGATTTACAAGATCTCTTACTATTTA
TACAACAAATCAAACAATATAATATATTAACAGATCATAAAATTACACA
ATGTAATAATTATTATAAGGAAATCATAAAAATGAAAGAAGATATAAAT
CATATTCATATATATATACAACCAATTCTAAATAATTTACACACATTAA
AACAAGTACAAAATAATAAAATCAAATATGAAGAGCACATCAAACAAAT
ATTACAAAAAATTTATGATAAAAAGGAATCTTTAAAAAAAATTATTCTC
TTAAAAGATGAAGCACAATTAGACATTACCCTCCTCGATGACTTAATAC
AAAAGCAAACAAAAAAACAAACACAAACACAAACACAAACACAAAAACA
AACACTAATACAAAATAATGAGACGATTCAACTTATTTCTGGACAAGAA
GATAAACATGAATCCAATCCATTTAATCATATACAAACCTATATTCAAC
AAAAAGATACACAAAATAAAAACATCCAAAATCTTCTTAAATCCTTGTA
TAATGGAAATATTAACACATTCATAGACACAATTTCTAAATATATATTA
AAACAAAAAGATATAGAATTAACACAACACGTTTATACAGACGAAAAAA
TTAATGATTATCTTGAAGAAATAAAAAATGAACAAAACAAAATAGATAA
GACCATCGACGATATAAAAATACAAGAAACATTAAAACAAATAACTCAT
ATTGTTAACAATATAAAAACCATCAAAAAGGATTTGCTCAAAGAATTTA
TTCAACATTTAATAAAATATATGAACGAAAGATATCAGAATATGCAACA
GGGTTATAATAATTTAACAAAT
```

SEQ ID NO: 8 refer to the polypeptide sequence of a smaller PfRH1-RII (RII-3) fragment having deletion at the 5' and the 3' end.

LQIVQQKLLEIKQKKNDITHKVQLINHIYKNIHDEILNKKNNEITKII

INNIKDHKKDLOLLLFIQQIKQYNILTDHKITQCNNYYKEIIKMKEDI

NHIHIYIQPILNNLHTLKQVQNNKIKYEEHIKQILQKIYDKKESLKKI

ILLKIDEAQLDITLLDDLIQKQTKKQTQTQTQTQKQTLIQNNETIQLI

SGQEDKHESNPFNHIQTYIQQKDTQNKNIQNLLKSLYNGNINTFIDTI

SKYILKQKDIELTQHVYTDEKINDYLEEIKNEQNKIDKTIDDIKIQET

LKQITHIVNNIKTIKKDLLKEFIQHLIKYMNERYQNMQQGYNNLTN

Primer Sequences:

SEQ ID NO: 9 (5' GACCAGCTGGAATTTAGCCAT-GAACAGGAA 3') refers to the forward primer and SEQ ID NO: 10 refers to the reverse primer (5'AACGGGC-CCTTTTGTTTG CTTTTGTATTAA 3') used to amplify the Region I (RI) of *P. falciparum* PfRH1 (PfRH1-RI).

SEQ ID NO: 11 (5' GACCAGCTGAAAGATG-TAATAAATAATAAG 3') refers to the forward primer and SEQ ID NO: 12 refers to the reverse primer (5' AACGGGC-CCATTTAA TATTTTTAAAATTTT 3') used to amplify the Region II (RII) of *P. falciparum* PfRH1 (PfRH1-RII).

SEQ ID NO: 13 (5' TCTCGTCAGCTGCTAATA-CAAAATAATGAGACG 3') refers to the forward primer and SEQ ID NO: 14 refers to the reverse primer (5' ACGATGGGGCC CTATATCGTCAAAATGTTTTGT 3') used to amplify the Region III (RIII) of *P. falciparum* PfRH1 (PfRH1-RIII).

SEQ ID NO: 15 (5' GACCAGCTGATATCCT-TAAAAGCTTGTGAA 3') refers to the forward primer and SEQ ID NO: 16 refers to the reverse primer (5' AACGGGC-CCTTTAGA TTTGTTTACATCTAT 3') used to amplify the Region IV (RIV) of *P. falciparum* PfRH1 (PfRH1-RIV).

SEQ ID NO: 17 (5' GACCAGCTGTACCATGCTGAT-GATACACGT 3') refers to the forward primer and SEQ ID NO: 18 refers to the reverse primer (5' AACGGGC-CCTATAAA AACATTATATATTTC 3') used to amplify the Region V (RV) of *P. falciparum* PfRH1 (PfRH1-RV).

SEQ ID NO: 19 (5' GACCAGCTGAATAATGCTCAAC-TATATTTT 3') refers to the forward primer and SEQ ID NO: 20 refers to the reverse primer (5' AACGGGCCCATTCAT TTGTTCTAATTTGTT 3') used to amplify the Region VI (RVI) of *P. falciparum* PfRH1 (PfRH1-RVI).

SEQ ID NO: 21 (5' GACCAGCTGCAATCATATAATT-TAATACAA 3') refers to the forward primer and SEQ ID NO: 22 refers to the reverse primer (5' AACGGGCCCGATGTT GGTTATAT TTCTTG 3') used to amplify the Region VII (RVII) of *P. falciparum* PfRH1 (PfRH1-RVII).

SEQ ID NO: 23 (5' GACCAGCTGACAATAATTAAT-CAAAGTATA 3') refers to the forward primer and SEQ ID NO: 24 refers to the reverse primer (5' AACGGGCCC ATTTTTTTTTTGTTCAATTC 3') used to amplify the Region VIII (RVIII) of *P. falciparum* PfRH1 (PfRH1-RVIII).

SEQ ID NO: 25 (5' TCTCGTCAGCTGAAAGATG-TAATAAATAATAAG 3') refers to the forward primer and SEQ ID NO: 26 (5' AACGGG CCCATTTGTTAAATTAT-TATAACC 3') refers to the reverse primer used to amplify the smaller fragment of Region II (RII-1) of *P. falciparum* PfRH1 (PfRH1-RII-1).

SEQ ID NO: 27 (5' GACCAGCTGTTACAAATAGTA-CAACAAAAA 3') refers to the forward primer and SEQ ID NO: 28 (5' AACGGGCCCATTTAATATTTTTAAAATTTT 3') refers to the reverse primer used to amplify the smaller fragment of Region II, (RII-2) of *P. falciparum* PfRH1 (PfRH1-RII-2).

SEQ ID NO: 29 (5' GACCAGCTGTTACAAATAGTA-CAACAAAAA 3') refers to the forward primer and SEQ ID NO: 30 (5' AACGGGCCC ATTTGTTAAATTATTATAACC 3') refers to the reverse primer used to amplify the smaller fragment of Region II, (RII-3) of *P. falciparum* PfRH1 (PfRH1-RII-3).

SEQ ID NO: 31 (5' CGT ATACTCGAGATGGGGGG-GACTGCCGCC 3') refers to the universal forward primer and SEQ ID NO: 32 (5' CGTATAGGATC CAAGTAAAA-CAAGGGCTG 3') refers to the universal reverse primer used to amplify the various regions (RI to RVIII) cloned into pRE4 vector for sub cloning of the respective regions into the pEGFP-N1 vector.

SEQ ID NO: 33 (5' GACCATATGTTACAAATAGTA-CAACAAAAA 3') refers to forward primer and SEQ ID NO: 34 (5' AACCTCGAGATTTGT TAAATTATTATAACC 3') refers to reverse primer used to amplify the smaller fragment of Region II, (RII-3) for cloning into pET24a+ over expres-sion vector.

SEQ ID NO: 35 (5' GACGAATTCATAAATGAA-GAAGCTCTACAA 3') refers to forward primer and SEQ ID NO: 36 (5' AACCTCGAGATTTTTTTT TTTGTTCAATTC 3') refers to reverse primer used to amplify the smaller fragment of Region VIII, (rtRVIII) for cloning into pET24a+ over expression vector.

SEQ ID NO:37: DNA sequence of rtRVIII

ATAAATGAAGAAGCTCTACAATTTCACAGGCTCTATGGACACAATCTTA
TAAGTGAAGATGACAAAAATAATTTGGTACATATTATAAAAGAACAAAA
GAATATATATACACAAAAGGAAATAGATATTTCTAAAATAATTAAACAT
GTTAAAAAAGGATTATATTCATTGAATGAACATGATATGAATCATGATA
CACATATGAATATAATAAATGAACATATAAATAATAATATTTTACAACC
ATACACACAATTAATAAACATGATAAAAGATATTGATAATGTTTTTATA
AAAATACAAAATAATAAATTCGAACAAATACAAAAATATATAGAAATTA
TTAAATCTTTAGAACAATTAAATAAAAATATAAACACAGATAATTTAAA
TAAATTAAAAGATACACAAAACAAATTAATAAATATAGAAACAGAAATG
AAACATAAACAAAAACAATTAATAAACAAAATGAATGATATAGAAAAGG
ATAATATTACAGATCAATATATGCATGATGTTCAGCAAAATATATTTGA
ACCTATAACATTAAAAATGAATGAATATAATACATTATTAAATGATAAT
CATAATAATAATATAAATAATGAACATCAATTTAATCATTTAAATAGTC
TTCATACAAAAATATTTAGTCATAATTATAATAAAGAACAACAACAAGA
ATATATAACCAACATCATGCAAAGAATTGATGTATTCATAAATGATTTA
GATACTTACCAATATGAATATTATTTTTATGAATGGAATCAAGAATATA
AACAAATAGACAAAAATAAAATAAATCAACATATAAACAATATTAAAAA
TAATCTAATTCATGTTAAGAAACAATTTGAACACACCTTAGAAAATATA
AAAAATAATGAAAATATTTTCGACAACATACAATTGAAAAAAAAAGATA
TTGACGATATTATTATAAACATTAATAATACAAAAGAAACATATCTAAA
AGAATTGAACAAAAAAAAAAAT

Figure 5:
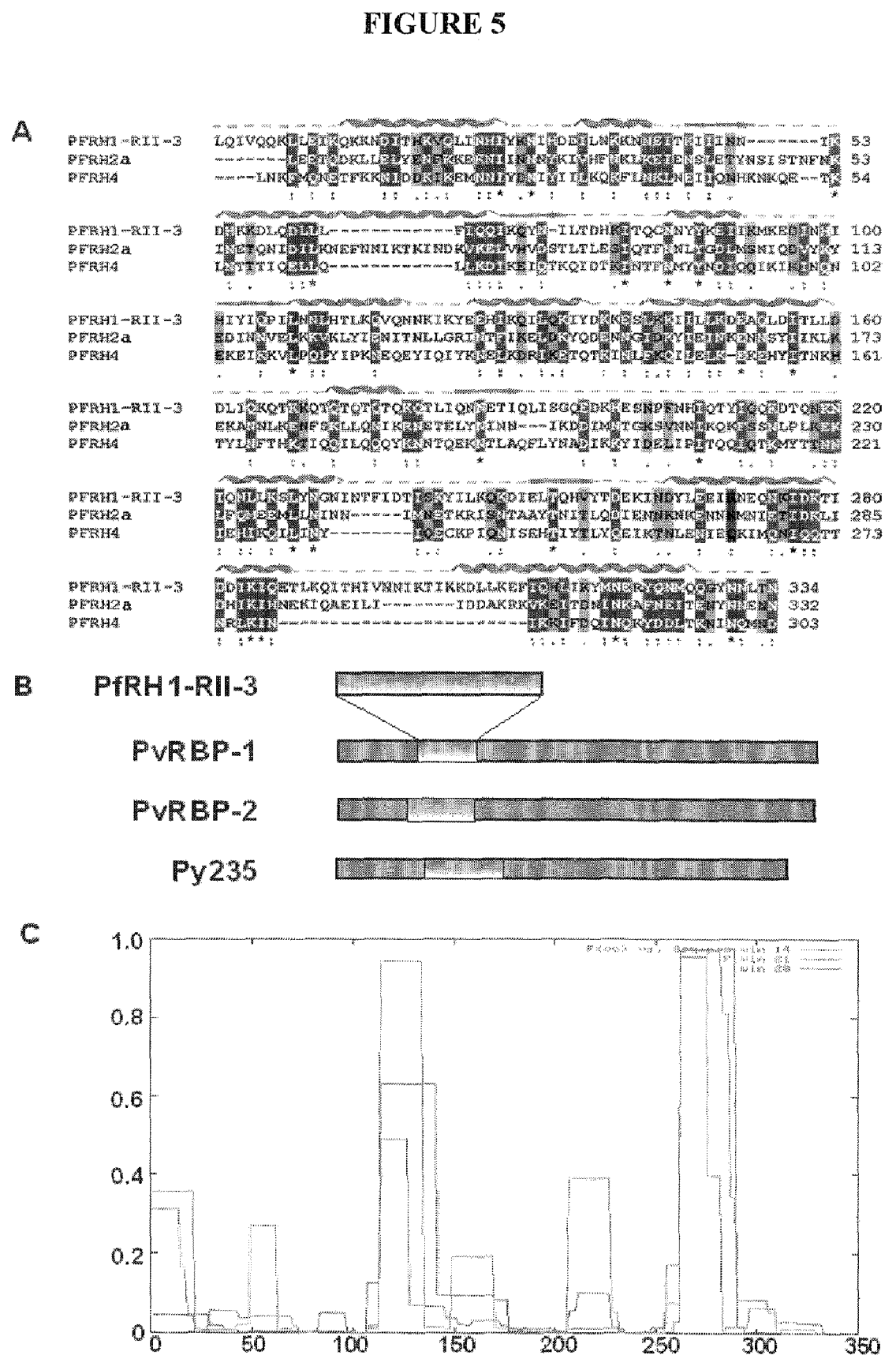

Homologous Sequences (FIGS. 5 and 6):

SEQ ID NO: 38 refers to the PfRH2a sequence homologous to the PfRH1-RII-3 binding domain.

LEETQDKLLELYENFKKEKNIINNNYKIVHFNKLKEIENSLETYNSIST
NFNKINETQNIDILKNEFNNIKTKINDKVKELVHVDSTLTLESIQTFNN
LYGDLMSNIQDVYKYEDINNVELKKVKLYIENITNLLGRINTFIKELDK
YQDENNGIDKYIEINKENNSYIIKLKEKANNLKENFSKLLQNIKRNETE
LYNINNIKDDIMNIGKSVNNIKQKFSSNLPLKEKLFQMEEMLLNINNIM
NETKRISNTAAYTNITLQDIENNKNKENNNMNIETIDKLIDHIKIHNEK
IQAEILIIDDAKRKVKEITDNINKAFNEITENYNNENN

SEQ ID NO: 39 refers to the sequence of the predicted binding region of P. falciparum PfRH2b.

LEETQDKLLELYENFKKEKNIINNNYKIVHENKLKEIENSLETYNSIST
NFNKINETQNIDILKNEENNIKTKINDKVKELVHVDSTLTLESIQTENN
LYGDLMSNIQDVYKYEDINNVELKKVKLYIENITNLLGRINTFIKELDK
YQDENNGIDKYIEINKENNSYIIKLKEKANNLKENFSKLLQNIKRNETE
LYNINNIKDDIMNTGKSVNNIKQKFSSNLPLKEKLFQMEEMLLNINNIM
NETKRISNTDAYTNITLQDIENNKNKENNNMNIETIDKLIDHIKIHNEK
IQAEILIIDDAKRKVKEITDNINKAFNEITENYNNENN

SEQ ID NO: 40 refer to the PfRH4 sequence homologous to the PfRH1-RII-3 binding domain.

LNKFMQNETFKKNIDDKIKEMNNIYDNIYIILKQKFLNKLNEIIQNHKN
KQETKLNTTTIQELLQLLKDIKEIQTKQIDTKINTFNMYYNDIQQIKIK
INQNEKEIKKVLPQLYIPKNEQEYIQIYKNELKDRIKETQTKINLEKQI
LELKEKEHYITNKHTYLNETHKTIQQILQQQYKNNTQEKNTLAQFLYNA
DIKKYIDELIPITQQIQTKMYTTNNIEHIKQILINYIQECKPIQNISEH
TIYTLYQEIKTNLENIEQKIMQNIQQTTNRLKINIKKIFDQINQKYDDL
TKNINQMND

SEQ ID NO: 41 refers to the predicted sequence of the binding region of P. falciparum PfRH3.

INEIKSKMDNINEKLKHITDFIDKNVNYIYENHSTQDINIMLNNTISEY
NKLEFINSDIEDNISKKLKKELQDLVTLKESLMKMNHNVLKMDPLKSLN
QVLEKYEELKKNINEYSKEENKLYDFKKQMESRLNAFITNLNNNDETLV
DGKNIYDQFVEYKEQLLIKKRIIINNEIVIINDEVKKIKDELKSYNILS
YKLENDTSHDVVNSVENTPSSDVATAVSNSSSILSTYNSTELNKLRNFF
SEKDDELNVESKVKQDENIFIEKNKIFDDIIKDIELYNKKTNAIKNLNN
AINGSMNNLSLIDSVMKNKGDIINRLSQRSYLIQTDNFIDIYEKIFLKD
NLNKGLEEIENRLSNTYMNELKIEAEKQNEKYKKLKENINTYDDTFLEK
LIGDNYEWEVLKIELNGLNVNYNILQANIDTLIIKPYIDHIDHIISLIE
SLKHNIENKIKKVIPNLERLKDFIQTKENTNDIKLDHNNLIT

SEQ ID NO: 42 refers to the predicted sequence of the binding region of P. vivax PvRBP-1.

INDLQDLIDQMKEYKDEIVNNSEFISNRYKNIYENLKETYETELNDIGK
LENDTSKVNFYLMQIRKINTEKTKIDESLQTVEKEYKEILDSKEKIYEL
KIEFEKSVTEINRLQDGESARDLHEEQIKEILDKMAKKVHYLKELLSLK
GKSSVYFTEMNELLNTASYDNMEGFSAKKEKADNDINALYNSVYREDIN
ALIEEVEKEVTENKESTLEMLKDEEMEEKLQDAKETFAKLNFVSDDKLT
DVYTKMSAEVTNAEGIKKEIAQKQFENVHKKMKEFSDAFSTKFEALQNS
MQQYNQEGD

SEQ ID NO: 43 refers to the predicted sequence of the binding region of P. vivax PvRBP-2.

LQKVESDIYRVELKTLFYVAAKHYADFKFSLEHLKMFENLSKSKEKMLY
STFEKLEGDLLNKINTLMGSEQSTSDLTSIIADSEKIIKSAESLINSSS
EEIAKYALDSNEKINFIKKNYDQNILKVREFINKSNGLITSVKGTSQLS
ESDKQQIETKIEEIKKKKKDILERGKEFINIMNEIKKKKKSNSSNSSTN

-continued

```
SKEFTDKLKELETEFEGLNKTVKGYLQEIEDIKVKENEDRSLKNQIEQH

LKYTSDNRDNVKTLISKNDEIQKYIEKIEKLINDAPSGKDKETTEKTNL

QNKVKKIIDEFHKEDLQLLLNSLSKFYEEHQKLYNEASTIEKIKDLHQK

TKEEYEKLEKMKESNEGQILDKLNTELDNLKTLEKNIVEEQTNYINKVM

SDSLTNLTAEVDNLRS
```

DETAILED DESCRIPTION OF THE INVENTION

Bibliographic references mentioned in the present specification are for convenience listed in the form of a list of references and added at the end of the examples. The whole content of such bibliographic references is herein incorporated by reference.

The binding of the merozoites to erythrocytes is mediated by specific binding proteins on the surface of the merozoite and is necessary for the erythrocyte invasion. At least two gene families the Reticulocyte Binding Protein homologues (RH) and the family of erythrocyte binding proteins/ligands (EBL) have been shown to mediate specific interactions with host cell receptors thereby defining host cell specificity and are thought to play an important role in parasite virulence and possibly immune evasion. How binding of EBL or RH to specific erythrocyte receptors ultimately leads to merozoite invasion is an important question. In particular, invasion of erythrocytes by malaria parasite *Plasmodium falciparum* depends on recognition of specific erythrocyte surface receptors by parasite ligands. The >300 kDa *P. falciparum* reticulocyte binding protein homologue 1 (PfRH1) recognizes a so far uncharacterized neuraminidase sensitive, trypsin resistant receptor on the surface of the erythrocyte. PfRH1 is a member of the reticulocyte binding protein homologues (RH) gene family which is found in all malaria species and plays an important role in host cell selection and virulence.

The inventors have further identified the corresponding regions in the *Plasmodium falciparum* and/or *P. vivax* orthologues (FIG. 6). They have also shown that the region elicits protective antibodies in mice (FIG. 7). Accordingly, the inventors demonstrated that immunization of mice with the correctly folded binding region of PfRH1 elicits strong invasion inhibitory antibodies while other regions of the same protein do not produce such inhibitory antibodies.

Although the invention will be described with specific reference to regions derived from *Plasmodium falciparum* and/or *P. vivax* orthologues, the invention is not limited to regions from only these two parasites. Any other homologous region derived from any other *Plasmodium* known in the art, for example, *Plasmodium ovale, Plasmodium malaria, Plasmodium yoelii, Plasmodium knowlesi, Plasmodium reichnowi, Plasmodium cynomolgi* or the like may be encompassed by the present invention.

The present invention provides isolated polypeptide fragments of Reticulocyte Binding Protein homologues, PfRH1, involved in the binding and/or invasion of the erythrocytes by *Plasmodium*.

Accordingly, there is provided an isolated polypeptide, wherein the polypeptide is a *Plasmodium* Reticulocyte Binding Protein homologue fragment, comprising, substantially comprising or consisting of at least one amino acid sequence selected from SEQ ID NO: 2, SEQ ID NO: 4, SEQ ID NO: 6 and SEQ ID NO: 8, a homologue or a portion thereof. The isolated polypeptide may comprise, substantially comprise or consist of at least one amino acid sequence selected from SEQ ID NO: 4, SEQ ID NO: 6 and SEQ ID NO: 8, a homologue and/or a portion thereof. In particular the at least one amino acid sequence may comprise, substantially comprise or consist of the sequence of SEQ ID NO: 8, a homologue and/or a portion thereof. The isolated polypeptide sequence may be less than 700 amino acids, in particular less than 550 amino acids. More in particular, the isolated polypeptide may comprise less than 400 or less than 350 amino acids. The isolated polypeptide may be selected from PfRH1, PvRBP1 and/or a homologue thereof.

According to another aspect, the invention provides an isolated polypeptide comprising, substantially comprising or consisting of at least one amino acid sequence selected from SEQ ID NO: 2, SEQ ID NO: 4, SEQ ID NO: 6 and SEQ ID NO: 8, a homologue or a portion thereof, wherein the polypeptide comprises less than 700. In particular, the polypeptide comprises less than 550 amino acids. More in particular, the isolated polypeptide may comprise less than 400 or less than 350 amino acids. More in particular, the polypeptide according to the invention consists of at least one amino acid sequence selected from SEQ ID NO: 2, SEQ ID NO: 4, SEQ ID NO: 6 and SEQ ID NO: 8, a homologue or a portion thereof.

The invention also provides an isolated polynucleotide encoding a polypeptide comprising at least one nucleic acid sequence selected from SEQ ID NO: 1, SEQ ID NO: 3, SEQ ID NO: 5 and SEQ ID NO: 7, a homologue and/or a portion thereof. In particular, the polynucleotide may comprise at least one nucleic acid sequence selected from SEQ ID NO: 3, SEQ ID NO: 5 and SEQ ID NO: 7, a homologue and/or a portion thereof. More in particular the at least one nucleic acid sequence may be SEQ ID NO: 7, a homologue and/or a portion thereof.

With the term "comprising" it is understood that the polypeptide and/or polynucleotide according to the invention comprises at least one indicated sequences (for example a specific sequence indicated with a SEQ ID Number or an homologous sequence or fragment thereof) plus an additional (fixed, variable or chosen) sequence at the 5' end and/or at the 3' end of the claimed sequence.

With the term "substantially comprising" it is understood that the polypeptide and/or polynucleotide according to the invention "substantially" comprises the indicated sequence as "essential" element. Additional sequences may be included at the 5' end and/or at the 3' end. Accordingly, a polypeptide "substantially comprising" sequence X will be novel in view of a known polypeptide accidentally comprising the sequence X.

With the term "consisting of" it is understood that the polypeptide and/or polynucleotide according to the invention corresponds to at least one of the indicated sequence (for example a specific sequence indicated with a SEQ ID Number or an homologous sequence or fragment thereof).

In the present description, the polypeptide, polynucleotide, composition or other products according to the invention will be generally indicated to "comprise" a sequence. However, for the purpose of the present application the use of the term "comprise" will also include the optional limitation "substantially comprise" or "consist of".

The term "nucleic acid" is well known in the art and is used to generally refer to a molecule (one or more strands) of DNA, RNA or a derivative or analog thereof comprising nucleobases. A nucleobase includes, for example, a purine or pyrimidine base found in DNA (e.g., an adenine "A", a guanine "G", a thymine "T" or a cytosine "C") or RNA (e.g., an A, a G, an Uracil "U" or a C). The term nucleic acid encompasses the terms "oligonucleotide" and "polynucleotide" each as subgenus of the term "nucleic acid". The term "complementary" in the context of nucleic acids refers to a strand of nucleic acid non-covalently attached to another strand, wherein the complementarity of the two strands is defined by the complementarity of the bases. For example, the base A on one strand pairs with the base T or U on the other, and the base G on one strand pairs with the base C on the other. An oligonucleotide or analog is of "substantial complementarity" when there is a sufficient degree of complementarity to avoid non-specific binding of the oligonucleotide or analog to non-target sequences under conditions in which specific binding is desired.

The term "isolated" as used herein refers to a biological component (such as a nucleic acid, peptide or protein) that has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been isolated thus include nucleic acids and proteins purified by standard purification methods. The term also embraces nucleic acids, peptides and proteins prepared by recombinant expression in a host cell as well as chemically synthesized nucleic acids. A "nucleotide" Includes, but is not limited to, a monomer that includes a base linked to a sugar, such as a pyrimidine, purine or synthetic analogs thereof, or a base linked to an amino acid, as in a peptide nucleic acid (PNA). "Polynucleotide" refers to a nucleic acid sequence (such as a linear sequence) of any length. Therefore, a polynucleotide includes oligonucleotides, and also gene sequences found in chromosomes. Accordingly a nucleotide is one monomer in a polynucleotide. A nucleotide or nucleic acid sequence refers to the sequence of bases in a polynucleotide.

A "polypeptide" is a polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "polypeptide fragment" refers to a portion of a polypeptide which exhibits at least one useful epitope. An "epitope" is a region of a polypeptide capable of binding an immunoglobulin generated in response to contact with an antigen.

"Homologues" of a nucleotide or amino acid sequence will possess a relatively high degree of sequence identity or homology when aligned using standard methods. Methods of alignment of sequences for comparison are well known in the art. Homologues of a nucleotide or amino acid sequence of the PfRH binding region, in particular the homologues of SEQ ID NO: 2, SEQ ID NO: 4, SEQ ID NO: 6, and SEQ ID NO: 8 are typically characterized by possession of at least 75%, for example at least 85%, 90%, 95%, 98%, or 99%, sequence identity counted over the full length alignment with the originating NS sequence using the NCBI Blast 2.0, set to default parameters. Methods for determining sequence identity over such short windows are available at the NCBI website on the Internet. One of skill in the art will appreciate that these sequence identity ranges are provided for guidance only; it is entirely possible that strongly significant homologues could be obtained that fall outside of the ranges provided. An RH "fragment" as used herein, is meant to cover any nucleotide or amino acid sequence derived from the RH nucleotide or amino acid sequence known in the art. The derived RH "fragment" is shorter by at least one nucleotide or one amino acid compared to the RH sequence known in the art. In particular the RH protein "fragment" may be 700 amino acids in length. More in particular the RH protein "fragment" may be 550 amino acids in length.

Any of the isolated polynucleotide described above may be comprised in a vector. The vector may be comprised in a cell. Accordingly there is provided a method of producing the polypeptide according to any one of embodiment of the invention, the method comprising the steps of:

(a) culturing the cell according to the invention, under conditions suitable for expression of the polypeptide; and
(b) recovering the polypeptide so expressed.

The recovered polypeptide may comprise at least one of the amino acid sequence selected from SEQ ID NO: 2, SEQ ID NO: 4, SEQ ID NO: 6 and SEQ ID NO: 8, a homologue and/or a portion thereof. The at least one amino acid sequence may comprise the sequence of SEQ ID NO: 8, a homologue and/or a portion thereof.

A "vector" refers to a nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins (e.g. the polypeptides of the present invention) other than those native to the cell. A vector optionally includes materials to aid in achieving entry of the nucleic acid into the cell, such as a viral particle, liposome, protein coating or the like.

Unless otherwise explained, all technical and scientific terms used herein have the same meaning as commonly understood by one of ordinary skill in the art. It is further to be understood that all base pair sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described. The term "comprises" means "includes."

According to another aspect the invention provides an isolated antibody, wherein the antibody specifically binds to polypeptide comprising at least one amino acid sequence selected from SEQ ID NO: 2, SEQ ID NO: 4, SEQ ID NO: 6 and SEQ ID NO: 8, a homologue and/or a portion thereof. In particular, the antibody specifically binds to a polypeptide comprising the amino acid sequence of SEQ ID NO: 2 and SEQ ID NO: 8 a homologue and/or a portion thereof. The antibody may be a monoclonal, polyclonal, chimeric, humanised, single chain, Fab, Fab', F(ab)' fragments and/or F(v) portions of the whole antibody.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a *Plasmodium* PfRHI-RII. For example, antibody fragments capable of binding to PfRHI-RII and/or portions thereof, include, but not limited to Fab (e.g., by papain digestion), Fab' (e.g., by pepsin digestion and partial reduction) and F (ab') 2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention.

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F (ab') 2 heavy chain portion can be designed to include DNA sequences encoding the CH1 domain and/or hinge region of the heavy chain. The various portions of antibodies can be joined together chemically by conventional techniques, or can be prepared as a contiguous protein using genetic engineering techniques.

"Polyclonal antibodies" are antibodies that are derived from different B-cell lines. They are a mixture of immunoglobulin molecules secreted against a specific antigen, each recognising a different epitope. Many methodologies exist for polyclonal antibody production in laboratory animals. Institutional guidelines governing animal use and procedures relating to these methodologies are generally oriented around humane considerations and appropriate conduct for adjuvant (agents which modify the effect of other agents while having few if any direct effects when given by themselves) use. This includes adjuvant selection, routes and sites of administration, injection volumes per site and number of sites per animal. Institutional policies generally include allowable volumes of blood per collection and safety precautions including appropriate restraint and sedation or anesthesia of animals for injury prevention to animals or personnel.

The primary goal of antibody production in laboratory animals is to obtain high titer, high affinity antibodies from the serum of animals following immunization with the antigens. Adjuvants are used to improve or enhance an immune response to antigens. Most adjuvants provide for an injection site, antigen depot which allows for a slow release of antigen into draining lymph nodes. Production of polyclonal antibodies is well known in the art.

By contrast, "monoclonal antibodies" are derived from a single cell line and the antibodies are produced by the hybridoma technology well known to those skilled in the art.

According to a further aspect, the invention provides a pharmaceutical composition for reducing and/or inhibiting the binding to and/or invasion of *Plasmodium* into erythrocytes, comprising
  (a) at least one antibody and/or portion thereof, capable of binding to at least one amino acid sequence selected from SEQ ID NO: 2, SEQ ID NO: 4, SEQ ID NO: 6 and SEQ ID NO: 8, a homologue or a portion thereof; or
  (b) at least one polypeptide comprising at least one amino acid sequence selected from SEQ ID NO:2, SEQ ID NO: 4, SEQ ID NO: 6 and SEQ ID NO: 8, a homologue and/or a portion thereof; and/or
  (c) at least one nucleic acid molecule hybridizing and/or complementary to any part of the polynucleotide comprising at least one nucleic acid sequence selected from SEQ ID NO: 1, SEQ ID NO: 3, SEQ ID NO: 5 and SEQ ID NO: 7, a homologue and/or a portion thereof optionally in the presence of at least one pharmaceutically acceptable excipient, diluent, carrier, additive, adjuvant and/or a combination thereof. The pharmaceutical composition is a pharmaceutical composition formulated for reducing and/or inhibiting the binding to and/or invasion of *Plasmodium* into erythrocytes. The pharmaceutical composition may be in the presence of at least one pharmaceutically acceptable carrier, diluent, excipient additive and/or adjuvant. Examples of suitable excipients are water, saline, dextrose, glycerol, ethanol and the like as well as combinations thereof. Such a pharmaceutical composition may consist of the active ingredient alone, in a form suitable for administration to a subject, or alternatively the pharmaceutical composition may comprise the active ingredient and one or more pharmaceutically acceptable carrier, excipient and/or diluent. Excipients normally employed for such formulations, includes mannitol, lactose, starch, magnesium stearate, sodium saccharine, cellulose, magnesium carbonate, and the like. In particular, the pharmaceutical composition is useful for treating at least one condition selected from a group comprising of, cancer, infectious diseases, inflammatory diseases and autoimmune diseases. Accordingly, any pharmaceutical composition comprising a drug, compound, or substance capable of reducing and/or inhibiting the binding to and/or invasion of *Plasmodium* into erythrocytes is within the scope of the present invention.

The "pharmaceutical compositions" referred to herein, are preferably prepared and administered in dose units. For treatment of a subject, such as but not limited to a human subject, and depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administrations of subdivided doses at specific intervals. The pharmaceutical compositions can be administered systemically. The compositions are in general administered topically, intravenously, intramuscularly, orally, parenterally, or as implants, but even rectal use is possible in principle.

Suitable solid or liquid pharmaceutical preparation forms are, for example, granules, powders, tablets, coated tablets, (micro) capsules, suppositories, syrups, emulsions, suspensions, creams, aerosols, drops or injectable solutions in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. In certain embodiments patients with malaria may be treated with the polypeptides and/or polynucleotides of the invention or other specific blocking agents (e.g. monoclonal antibodies) thus preventing the binding of the *plasmodium* merozoites to the erythrocyte surface and/or their invasion into the erythrocytes.

The polynucleotides mentioned herein are for reducing and/or inhibiting the binding to and/or invasion of *Plasmodium* into erythrocytes. Accordingly, the method comprises administering to or transfecting in vivo or in vitro the cells with a nucleic acid construct comprising a nucleic acid molecule and/or hybridising to and/or complementary to any part of the polynucleotide comprising at least one nucleic acid sequence selected from SEQ ID NO: 1, SEQ ID NO:3, SEQ ID NO: 5 and SEQ ID NO: 7, a homologue and/or a portion thereof.

The present invention therefore extends to the preparation of anti-sense nucleotides, ribozymes and silencing interference RNA (siRNA) technology that may be used to interfere with the expression of SEQ ID NO: 1, SEQ ID NO:3, SEQ ID NO: 5 and SEQ ID NO: 7, a homologue and/or a portion thereof. This approach involves anti-sense nucleic acid molecules and ribozymes to block expression, either by masking it with an anti-sense nucleic acid or cleaving it with a ribozyme.

Anti-sense nucleic acids are DNA or RNA molecules that are complementary to at least a portion of a specific mRNA molecule. In the cell, they hybridise to that mRNA, forming an untranslatable double-stranded molecule. Therefore, anti-sense nucleic acids interfere with the expression of mRNA into protein. Anti-sense methods have been used to inhibit the expression of many genes in vitro. The reduction and/or inhibition of binding to an/or invasion of plasmodium into erythrocytes can also be carried out by the silencing interference RNA (siRNA) technology. RNA interference technology is well known and consists of a process in which a double stranded RNA (dsRNA) induces the postranscriptional degradation of homologous transcripts. RNAi can be initiated by exposing cells to dsRNA either via transfection or endogenous expression. According to the exemplified embodiment, DNA targeting sequences, are selected and prepared according to standard technology, for example, the DNA targeting sequence are generated using Ambion siRNA target finder on the world wide web at (ambion.com/techlib/misc/siRNA_finder.html). The DNA targeting sequences may be inserted into a construct and/or vector and used to transfect the cell or cell lines in vitro or in vivo. The RNA polymerase of the cell transcribes the siRNAs complementary to the SEQ ID NO: 1, SEQ ID NO:3, SEQ ID NO: 5 and SEQ ID NO: 7, a homologue and/or a portion thereof. These siRNAs form a complex known as the RNA-induced silencing complex or RISC which functions in homologous target RNA destruction. In mammalian systems, the sequence-specific RNAi effect has been observed by the introduction of siRNAs either via transfection or endogenous expression of 19-23 base transcripts capable of forming duplexes, or via expression of short hairpin RNAs. The siRNA expression constructs and/or vectors may be constructed according to any method known in the art, for example by chemical synthesis, in vitro transcription, by digestion of long dsRNA by an RNase III family enzyme (e.g. Dicer, RNase III), by expression in cells from an siRNA expression plasmid or viral vector, and expression in cells from a PCR-derived siRNA expression cassette. The construct is directly transfected into mammalian cells resulting in functional expression of siRNAs.

Accordingly, there is provided a method of treating and/or preventing malaria comprising administering to a subject in need a composition comprising
 (a) at least one antibody and/or portion thereof, capable of binding to at least one amino acid sequence selected from SEQ ID NO: 2, SEQ ID NO: 4, SEQ ID NO: 6 and SEQ ID NO: 8, a homologue or a portion thereof; and/or
 (b) at least one polypeptide comprising at least one amino acid sequence selected from SEQ ID NO:2, SEQ ID NO: 4, SEQ ID NO: 6 and SEQ ID NO: 8, a homologue and/or a portion thereof; and/or
 (c) at least one nucleic acid molecule hybridizing and/or complementary to any part of the polynucleotide comprising at least one nucleic acid sequence selected from SEQ ID NO: 1, SEQ ID NO: 3, SEQ ID NO: 5 or SEQ ID NO: 7, a homologue and/or a portion thereof.

The method may comprise reducing and/or inhibiting the binding to and/or invasion of *Plasmodium* into erythrocytes. The subject in need of the treatment may be a mammal, in particular a human. The method further comprises administering a composition which binds or interacts with the polynucleotide to reduce and/or inhibit the expression of binding domain polypeptide, namely the PfRH polypeptide. The composition may further comprise the polypeptides of the invention capable of binding to and blocking the erythrocyte receptor, thus preventing the binding of the polypeptides on the meroziote surface to the erythrocytes. The composition may alternatively comprise antibodies capable of binding to the polypeptides on the merozoite surface thus neutralizing the binding of the meroziotes to the erythrocyte surface blocking invasion. Increasing the concentration of the antibody or the polypeptide will act as antagonists, preventing the binding of the parasite to the erythrocyte.

A nucleic acid molecule is "hybridisable" to another nucleic acid molecule, when a single-stranded form of the nucleic acid molecule can anneal to the other nucleic acid molecule under the appropriate conditions of temperature and solution ionic strength (Sambrook and Russell, 2001). The conditions of temperature and ionic strength determine the "stringency" of the hybridisation. Hybridisation requires the two nucleic acids to contain complementary sequences. Depending on the stringency of the hybridisation, mismatches between bases are possible. The appropriate stringency for hybridising nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridisation decreases in the following order: RNA:RNA, DNA:RNA, DNA:DNA. For hybrids of greater than 100 nucleotides in length, equations for calculating Tm have been derived (Sambrook and Russell, 2001). For hybridisation with shorter nucleic acids, i.e. oligonucleotides, the position of mismatches becomes more important, and the length of the oligonucleotide determines its specificity (Sambrook and Russell, 2001).

At least one antibody of the invention binds at least one specified epitope specific to at least one peptide sequence, subunit, fragment, portion or any combination thereof as described herein. The at least one epitope can comprise at least one antibody binding region that comprises at least one portion of the protein sequences corresponding to the peptide sequences SEQ ID NO: 2, SEQ ID NO: 4, SEQ ID NO: 6 and SEQ ID NO: 8 as described herein.

According to a further aspect there is provided a use of
 (a) at least one antibody and/or portion thereof, capable of binding to at least one amino acid sequence selected from SEQ ID NO: 2, SEQ ID NO: 4, SEQ ID NO: 6 and SEQ ID NO: 8, a homologue or a portion thereof; and/or
 (b) at least one polypeptide comprising at least one amino acid sequence selected from SEQ ID NO:2, SEQ ID NO: 4, SEQ ID NO: 6 and SEQ ID NO: 8, a homologue and/or a portion thereof; and/or
 (c) at least one nucleic acid molecule hybridizing and/or complementary to any part of the polynucleotide comprising at least one nucleic acid sequence selected from SEQ ID NO: 1, SEQ ID NO: 3, SEQ ID NO: 5 and SEQ ID NO: 7, a homologue and/or a portion thereof.
in preparation of a medicament for use in therapy. The polypeptides comprising the sequence of SEQ ID NO:2, SEQ ID NO: 4, SEQ ID NO: 6 and SEQ ID NO: 8, a homologue and/or a portion thereof, the polynucleotides comprising the sequence of SEQ ID NO:1, SEQ ID NO: 3, SEQ ID NO: 5 and SEQ ID NO: 7, a homologue and/or a portion thereof or the antibody capable of binding to polypeptides comprising the sequence of SEQ ID NO:2, SEQ ID NO: 4, SEQ ID NO: 6 and SEQ ID NO: 8, a homologue and/or a portion thereof may be used in therapy. The use may be for treating and/or preventing malaria, wherein the use may be for reducing and/or inhibiting the binding to and/or invasion of *Plasmodium* into erythrocytes.

The phrase "reducing and/or inhibiting the binding to and/or invasion" used herein refers to the ability of the polypeptides or antibodies and/or nucleic acid molecules described in the previous section, to measurably reduce and/or inhibit ability of the *Plasmodium* parasite in making contact with the erythrocyte. In the present invention it contemplates blocking of the erythrocyte receptor by means of the polypeptides of the invention or blocking of the Reticulocyte Binding Protein homologue (ligand), for example the PfRH1, on the surface of the merozoite by means of the antibody. The invention further contemplates reduction and/or inhibition of the expression of the Reticulocyte Binding Protein homologue on the surface of *Plasmodium* merozoites by means of nucleic acids of the invention that are complementary and/or hybridisable to the nucleic acid and/or transcript sequences that transcribe and/or translate for the expression of the erythrocyte binding protein of the parasite. It is understood that the phrase is relative, and does not require absolute suppression. Thus, in certain aspects, reducing and/or inhibiting expression of the erythrocyte binding protein of the parasite requires that, following application of the nucleic acid molecules mentioned in the previous section, Reticulocyte Binding Protein homologue is expressed at least 5% less than prior to application these compounds and/or molecules, such as at least 10% less, at least 15% less, at least 20% less, at least 25% less, or even more reduced. Thus, in some particular aspects, application of the nucleic acid molecules inhibits and/or reduces expression of the protein by about 30%, about 40%, about 50%, about 60%, or more. In specific examples, where the nucleic acid molecules are particularly effective, expression is inhibited and/or reduced by 70%, 85%, 85%, 90%, 95%, or even more.

According to yet another aspect the invention provides a method of diagnosis and/or prognosis of malaria in a subject, comprising:
  (a) providing at least one sample from a subject;
  (b) detecting the presence of polynucleotide comprising at least one nucleic acid sequence selected from SEQ ID NO: 1, SEQ ID NO: 3, SEQ ID NO: 5 and SEQ ID NO: 7, a homologue and/or a portion thereof; and/or
  (c) detecting the presence of polypeptide comprising the amino acid sequence of SEQ ID NO: 2, SEQ ID NO: 4, SEQ ID NO: 6 or SEQ ID NO: 8, a homologue and/or a portion thereof;
wherein the presence of the polynucleotide and/or the polypeptide is indicative of presence of *Plasmodium* in the subject. The step c) may be in the presence of at least one antibody capable of binding to at least one polypeptide comprising the amino acid sequence selected from SEQ ID NO: 2, SEQ ID NO: 4, SEQ ID NO: 6 and SEQ ID NO: 8, a homologue and/or a portion thereof. The at least one polypeptide may comprise the amino acid sequence of SEQ ID NO: 8, a homologue and/or a portion thereof. The subject may be a mammal, in particular human. The invention also provides a diagnostic and/or prognostic kit for the diagnosis and/or prognosis of malaria in a subject comprising
  (a) at least one antibody and/or portion thereof, capable of binding to at least one amino acid sequence selected from SEQ ID NO: 2, SEQ ID NO: 4, SEQ ID NO: 6 and SEQ ID NO: 8, a homologue or a portion thereof; and/or
  (b) at least one nucleic acid molecule hybridizing and/or complementary to any part of the polynucleotide comprising at least one of the sequences selected from SEQ ID NO: 1, SEQ ID NO: 3, SEQ ID NO: 5 or SEQ ID NO: 7, a homologue and/or a portion thereof;
wherein the subject may be a mammal, in particular human.

A "subject" may be a patient suffering from malaria. A person skilled in the art will know how to select subjects based on their amenability to a particular treatment, or their susceptibility to a particular disease. The control for example, may not be suffering malaria. The control may not have detectable levels of the Reticulocyte Binding Protein homologue (polypeptide) and/or polynucleotide encoding for the protein (polypeptide) that may be indicative of presence of *Plasmodium* in the subject. The "control value" may also be an average value in obtained from a selected population.

"Diagnose" or "diagnosis" used herein, refers to determining the nature or the identity of malaria. A diagnosis may be accompanied by a determination as to the severity of the disease. "Prognostic" or "prognosis" used herein refers to predicting the outcome or prognosis of a disease, such as to give a chance of survival based on observations and results of clinical tests.

As used herein "presence of *plasmodium*" refers to a measurable parameter of the presence of the Reticulocyte Binding Protein homologue (polypeptide) and/or the polynucleotide encoding the protein (polypeptide). For example, presence of nucleic acids may be detected by the use of Southern blots, northern blots, in situ hybridization and/or quantitative real time PCR. The polypeptides of the invention can be detected using several well recognized binding assays, for example the COS cell binding assay described in the further sections. Further, labelled monoclonal antibodies to the polypeptides of the invention can be used to detect merozoites in the biological sample obtained from the subject. Alternatively, labelled polypeptides can be used to detect the presence of antibodies in the biological sample. Cell free assays can be used to measure the binding of the binding domain fragment of the current invention. For example, the erythrocyte proteins may be immobilized on a solid support and binding of labelled polypeptides may be measured. Various "means", for example, fluorometric, flow cytometric means may be used. The assays and means mentioned herein are examples, and by no way limiting.

According to yet another aspect, the present invention provides a method of inducing a protective immune response to *Plasmodium* merozoites in a subject comprising administering to the subject an immunologically effective amount of a pharmaceutical composition comprising at least one amino acid sequence selected from SEQ ID NO: 2, SEQ ID NO: 4, SEQ ID NO: 6 and SEQ ID NO: 8, a homologue and/or a portion thereof, in combination with pharmaceutically acceptable excipient, carrier and/or additive, optionally in the presence of an adjuvant. The at least one sequence may comprise the amino acid sequence of SEQ ID NO: 8, a homologue and/or a portion thereof. The method of inducing a protective immune response to *Plasmodium* merozoites may be in a subject wherein the subject may be a mammal, in particular human.

There is further provided a recombinant DNA vaccine comprising an expression vector for expression of a polynucleotide, comprising at least one nucleic acid sequence selected from SEQ ID NO: 1, SEQ ID NO: 3, SEQ ID NO: 5 and SEQ ID NO: 7, a homologue and/or a portion thereof, optionally in the presence of at least one pharmaceutically acceptable excipient, carrier and/or additive, optionally in the presence of an adjuvant. The at least one nucleic acid sequence may comprise the nucleic acid sequence of SEQ ID NO: 7, a homologue and/or a portion thereof. The polynucleotide in the recombinant may encode for an immunogenic peptide, comprising at least one of the amino acid sequence selected from SEQ ID NO: 2, SEQ ID NO: 4, SEQ ID NO: 6 and SEQ ID NO: 8, a homologue and/or a portion thereof. The at least one amino acid sequence may comprise the sequence of SEQ ID NO: 8, a homologue and/or a portion thereof. The recombinant vaccine may be for administration in a subject, wherein the subject may be a mammal, in particular human.

According to a further aspect the invention provides a method of vaccinating a patient against malaria comprising administering to the patient in need an effective amount of a recombinant DNA vaccine capable of expressing an immunogenic peptide comprising at least one amino acid sequence selected from SEQ ID NO: 2, SEQ ID NO: 4, SEQ ID NO: 6 and SEQ ID NO: 8, a homologue and/or a portion thereof after administration of the vaccine to a patient. The at least one amino acid sequence may comprise the sequence of SEQ ID NO: 8, a homologue and/or a portion thereof. The subject in need of the vaccine may be a mammal, in particular human.

The term "vaccine" is used herein to describe a preparation intended for active immunological prophylaxis (the protective effect which is preferably long-term, i.e., at least about 6 months and preferably, at least about one year or longer). In the present invention, vaccines comprise an expression vector, which expresses an antigenic protein after administration to a subject, such as a mammal. Vaccines may also comprise chimeric peptides or an immunogenic peptide portion thereof in combination with a signal peptide sequence and/or an anchor peptide sequence and optionally, additional antigenic peptides or immunogenic fragments thereof from *Plasmodium falciparum*. In alternative embodiments according to the present invention, the polypeptide or an immunogenic fragment thereof, is administered to a patient alone, but may be administered in combination with at least one additional immunogenic malaria peptide in combination with a pharmaceutically acceptable carrier, excipient or additive. The method of administering the vaccine (s) according to the present invention may vary and include intravenous, buccal, oral, transdermal and nasal, among others, but intramuscular or subcutaneous administration is the most common method of administration.

Methods of inducing an immunogenic response in a patient or vaccinating a patient against a malaria infection are also contemplated by the present invention. In this method, a patient is administered the polypeptides of the invention as an immunogenic fragment, thereof, alone or may be administered in combination with another merozoite surface or immunogenic fragment thereof in combination with a pharmaceutically acceptable carrier, excipient or additive at least once, or in certain instances, at selected intervals to provide a booster to the initial immunization or to maintain immunity in the treated patient for extended periods of time.

The immunogenic response generated preferably will be "substantially protective", i.e., will protect the patient from some of the more severe symptoms and physiological states of the malaria disease, including the death of the patient from malaria. The immune response may include the generation of antibodies; activation of cytotoxic T lymphocytes (CTL) against cells presenting peptides derived from the polypeptide sequences of the present invention, or other mechanisms well known in the art.

Having now generally described the invention, the same will be more readily understood through reference to the following examples which are provided by way of illustration, and are not intended to be limiting of the present invention.

EXAMPLES

Standard molecular biology techniques known in the art and not specifically described were generally followed as described in Sambrook and Russel, Molecular Cloning: A Laboratory Manual, Cold Springs Harbor Laboratory, New York (2001).

Generation of Constructs for Expression of Different Regions of PfRH1 on Surface of COS7 Cells The plasmid pRE4 (kindly given by Prof. John Adams, University of Notre Dame, Ind.) contains the gene for HSV gD. All constructs were designed to express eight different regions of PfRH1 fused to the secretory signal sequence and transmembrane domain of HSV gD (Chitnis et al, 1994). The pRE4 vector was digested with restriction enzymes PvuII and ApaI to excise the central region of HSV gD. The restriction fragments were separated by gel electrophoresis and the vector was recovered using QIAquick Gel Extraction Kit (Qiagen). *P. falciparum* 3D7 clone genomic DNA (gDNA) was used as a template for generating different regions of PfRH1 RI to RVIII. The 2 kb overlapping fragments of PfRH1 comprising the eight regions is shown in FIG. 1. The genomic DNA was extracted from infected blood using Easy DNA kit (Invitrogen). PCR primers were designed for generating ~2 Kb fragments with 1 Kb overlap according to 3D7 clone RH1 gDNA sequence with intro spliced out (Genbank accession no: AF533700). PCR products encoding different regions of PfRH1 were digested with PvuII and ApaI and in frame cloned into pRE4 to make the following constructs (I) to (VIII):

(I): SEQ ID NO: 9 and 10 were used to generate the region I of PfRH1 spanning the region from 55 to 2001 bp.
(II): SEQ ID NO: 11 and 12 were used to generate the region RII of PfRH1 comprising the sequence of SEQ ID NO: 1 spanning 1 the region from 1000 to 3000 bp. The SEQ ID NO: 2 comprises the polypeptide sequence encoded by SEQ ID NO: 1.
(III): SEQ ID NO: 13 and 14 were used to generate the region RIII of PfRH1 spanning the region from 2041 to 4002 bp.
(IV): SEQ ID NO: 15 and 16 were used to generate the region RIV of PfRH1 spanning the region from 3001 to 5001 bp.
(V): SEQ ID NO: 17 and 18 were used to generate the region RV of PfRH1 spanning the region from 4003 to 5000 bp.
(VI): SEQ ID NO: 19 and 20 were used to generate the region RVI of PfRH1 spanning the region from 5002 to 7002 bp.
(VII): SEQ ID NO: 21 and 22 were used to generate the region RVII of PfRH1 spanning the region from 6001 to 8001 bp.
(VIII): SEQ ID NO: 23 and 24 were used to generate the region RVIII of PfRH1 spanning the region from 7003 to 8301 bp.

The PCR products encoding the eight different regions of PfRH1 were digested with PvuII and ApaI and cloned in frame into pRE4. All the eight constructs of PfRH1 were then subcloned into pEGFP-N1 vector with flanking signal sequence and transmembrane domain from HSV gD so as to target the protein to the surface of transfected COS7 cells as a GFP fusion protein. Plasmid pEGFP-PvDBPII (kindly given by Prof. John Adams, University of Notre Dame, Ind.) was digested with XhoI and BamHI restriction enzymes to remove the DBPII. The pEGFP-N1 backbone was purified by gel electrophoresis and recovered using QIAquick Gel Extraction Kit (Qiagen). Universal primers were designed for generating eight GFP constructs of PfRH1 (primer [XhoI], 5' CGT ATACTCGAGATGGGGGGGACTGCCGCC 3'; (SEQ ID NO: 31); primer [BamHI], 5' CGTATAGGATC CAAG-TAAAACAAGGGCTG 3' (SEQ ID NO: 32). The amplified PCR fragments were cleaved with XhoI and BamHI and cloned into pEGFP-N1 vector digested by XhoI and BamHI restriction enzymes. All the GFP constructs were purified using QIAfilter plasmid Maxi Kit (Qiagen).

Erythrocyte Binding Assay and the Identification of Erythrocyte Binding Region of PfRH1.

Figure 2:
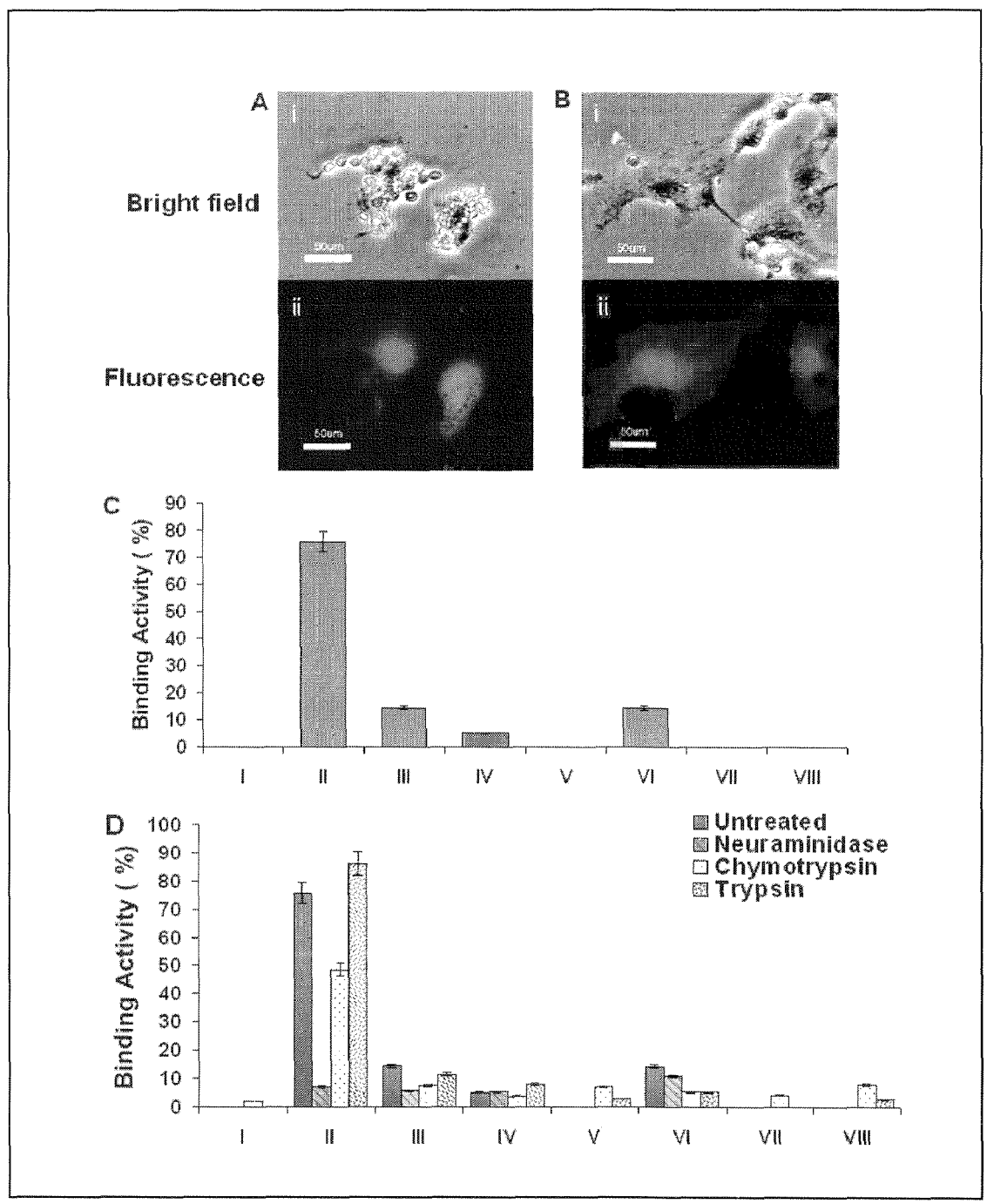
FIG. 2 represents the erythrocyte-binding assay on COS7 cells transfected with chimeric constructs, each expressing one of the eight regions of PfRH1 before and after enzymatic treatment. (A) Typical erythrocyte binding to COS cell expressing binding region or (B) non-binding region (magnification of X 200). (i) Bright field of typical field and corresponding (ii) Cell-associated fluorescence as GFP (green) Bar, 50 um. (C) Percentage (%) of erythrocyte binding activity of the various PfRH1 regions after normalizing transfection efficiency. (D) Comparison of Percentage (%) erythrocyte-binding activity of different regions of PfRH1 after enzymatic treatment. Data represent percentage of binding activity (%) after normalizing transfection efficiency to 5% in three independent experiments, and the error bar denotes the SE.

COS7 cells (American Type Culture Collection) were cultured and transfected with pEGFP constructs as described previously (Mayer et al, 2004). 2 kb overlapping fragments of PfRH1 as shown in FIG. 1, cloned into the mammalian cell expression vector, pEGFP-N1, generated GFP fusion proteins. The transfected cells were used for erythrocyte-binding assay 40-60 hours post-transfection by scoring the number of rossetes under an inverted fluorescent microscope (Nikon) as described previously (Chitnis et al, 1994). Transfected COS7 cells with at least half their surface area covered by erythrocytes were scored as positive for binding. The number of rosettes was counted in 30 fields at 200× magnification using an inverted fluorescent microscope. In each experiment, two wells of COS7 cells were transfected for each construct, and the data shown are from at least 3 separate experiments. The transfection efficiency (%) was calculated as total no. of fluorescent COS7 cells×100/total no. of COS7 cells, while binding activity (%) was calculated as total no. of fluorescent COS7 cells with rosettes×100/total no. of COS7 cells. The binding activity (%) was then normalized to 5% transfection efficiency. FIGS. 2A-ii and 2B-ii shows the binding of the erythrocytes as viewed under inverted fluorescent microscope. Region II (spanning the region from 1000 to 3000 bp) of PfRH1 possessed the strongest binding ability to erythrocytes with >70% binding activity (FIG. 2C). Regions III, IV and VI showed minimal binding (<10%) while no binding was observed in region I, V, VII and VIII of PfRH1 (FIG. 2C). Negative controls of either untransfected COS7 cells or COS7 cells expressing the *P. vivax* Duffy Binding Protein region II (PvDBPII) (Kind gift of Professor John Adams; Michon et al., 2000) with chymotrypsin-treated erythrocytes gave no rosettes. These data strongly suggested that region II of PfRH1 could be the erythrocyte binding region.

To further examine the specificity of erythrocyte binding to region II, we tested the ability of COS7 cells expressing all PfRH1 constructs to bind neuraminidase-, chymotrypsin- and trypsin-treated erythrocytes respectively. PfRH1 protein binds to a neuraminidase-sensitive, chymotrysin and trypsin-resistant receptor on the erythrocyte surface (Rayner et al, 2001). Human erythrocytes were collected in 10% citrate phosphate dextrose and stored at 4° C. for up to 4 weeks. The Duffy phenotypes of the erythrocytes were determined by a standard blood banking method (Chitnis et al, 1994). Duffy-positive human erythrocytes were washed 3 times in RPMI-1640 (Invitrogen) for use in erythrocyte-binding assay described above. Washed human erythrocytes were treated with neuraminidase, chymotrypsin and trypsin respectively as described previously (Rayner et al, 2001). In the current study binding of region II is dramatically affected when erythrocytes are pretreated with neuraminidase (FIG. 2D) with binding being reduced approximately 10 fold. Little or no impact on binding of erythrocytes to region II is seen when the erythrocytes are pretreated with chymotrypsin or trypsin (FIG. 2D). Enzyme treatment of erythrocytes had little impact on the minimal binding seen to any of the other regions (FIG. 2D). For all the experiments described the effectiveness of enzyme treatment was assessed by measuring the effect on binding of pretreated erythrocytes to COS7 cells expressing two known erythrocyte binding domains PvDBPII or EBA-175RII. Binding of erythrocytes to PvDBPII is known to be resistant to neuraminidase and trypsin treatment but sensitive to chymotrypsin while EBA-175RII is neuraminidase and trypsin sensitive but chymotrypsin resistant (Baum et al, 2003).

Taken together, these data clearly shows that RII of PfRH1 has the expected erythrocyte binding specificity previously demonstrated on the full length protein (Rayner et al, 2001). Generation of Constructs for Expression of Different Regions of PfRH1-RII on Surface of COS-7 Cells.

Similar methods as described above were used to express different regions of PfRH1-RII, namely RII-1, RII-2 and RII-3 (FIG. 3A) in pRE4 vector for expression on the surface of COS7 cells. Deletion constructs designed for pRE4 are described below as RII-1, RII-2, and RII-3. RII-1 contains region II DNA sequence 1 (SEQ ID NO: 3) from 1000 bp to 2499 bp (~1.5 Kb), but lacks ~500 bps at 3' end. RII-2 consists of region II DNA sequence (SEQ ID NO: 5) from 1498 bp to 3000 bp (~1.5 Kb), but lacks ~500 bps at 5' end. RII-3 contains region II DNA sequence (SEQ ID NO: 7) from 1498 bp to 2498 bp (1.0 Kb), but lacks ~500 bps at both ends. PCR primers SEQ ID NO: 25 and 26 were used to amplify the RII-1 region comprising the sequence of SEQ ID NO: 3. The SEQ ID NO: 3 encodes the polypeptide comprising SEQ ID NO: 3. PCR primers SEQ ID NO: 27 and 28 were used to amplify the RII-2 region comprising the sequence of SEQ ID NO: 5. The SEQ ID NO: 5 encodes the polypeptide comprising SEQ ID NO: 5. PCR primers SEQ ID NO: 29 and 30 were used to amplify the RII-3 region comprising the sequence of SEQ ID NO: 7. The SEQ ID NO: 7 encodes the polypeptide comprising SEQ ID NO: 7. The same primers were used to generate deletion constructs of region II as GFP fusion in pEGFP vector.

Identification of a Minimal Erythrocyte Binding Region of PfRH1

Figure 3:
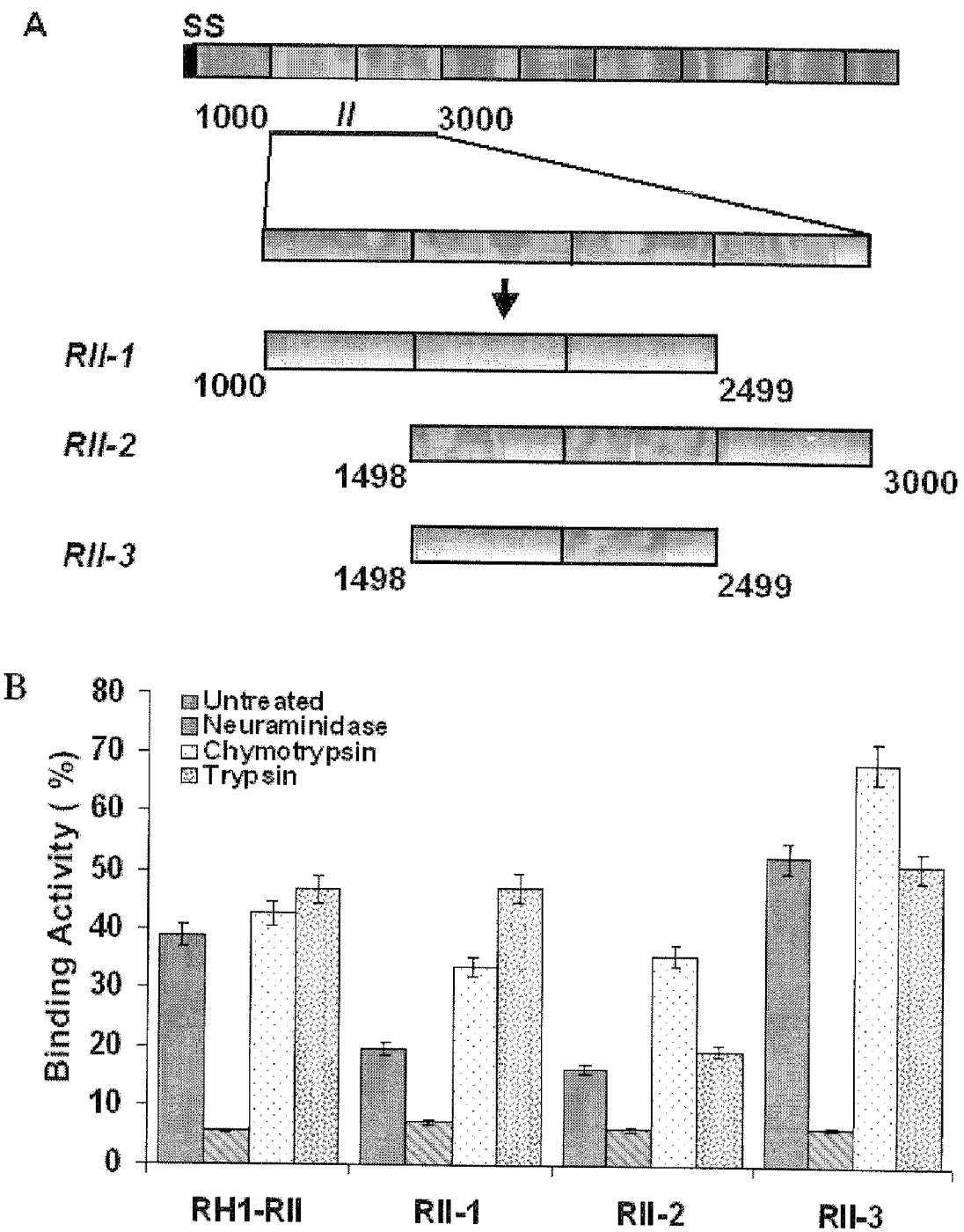
FIG. 3 represents erythrocyte-binding assay on COS7 cells transfected with construct expressing full-length region II or deletion constructs of PfRH1 before and after enzymatic treatment. (A) Overall architecture of Region II deletion constructs of PfRH1. RII-1 was deleted 500 bps at 3' end of region II, RII-2 was deleted 500 bps at 5' end of region II and RII-3 was deleted 500 bps at both ends of region II (light gray). (B). Comparison of erythrocyte-binding activity with full-length RII or deletion constructs before and after enzymatic treatment. Data represent percentage of binding activity (%) after normalizing transfection efficiency to 5% in three independent experiments, and the error bar denotes the SE.

To further delineate region II binding, the three deletion constructs RII-1, RII-2 and RII-3, cloned into pEGFP-N1 vector were transfected into in COS7 cells. Using the same approach as used for the larger construct strong binding was observed with the full-length region II, as well as the deletion constructs RII-1, RII-2 and RII-3 to erythrocytes (FIG. 3B). Neuraminidase treatment significantly decreased all binding activity while treatment with chymotrypsin or trypsin had little effect (FIG. 3B). RII-2 and RII-1 had a slightly reduced binding activity compared to full length RII, whereas RII-3 showed even better binding than RII. These data strongly suggest that RII-3 contains the minimal binding region of PfRH1.

Expression of rRII-3 and rtRVIII Recombinant Proteins

Figure 4:
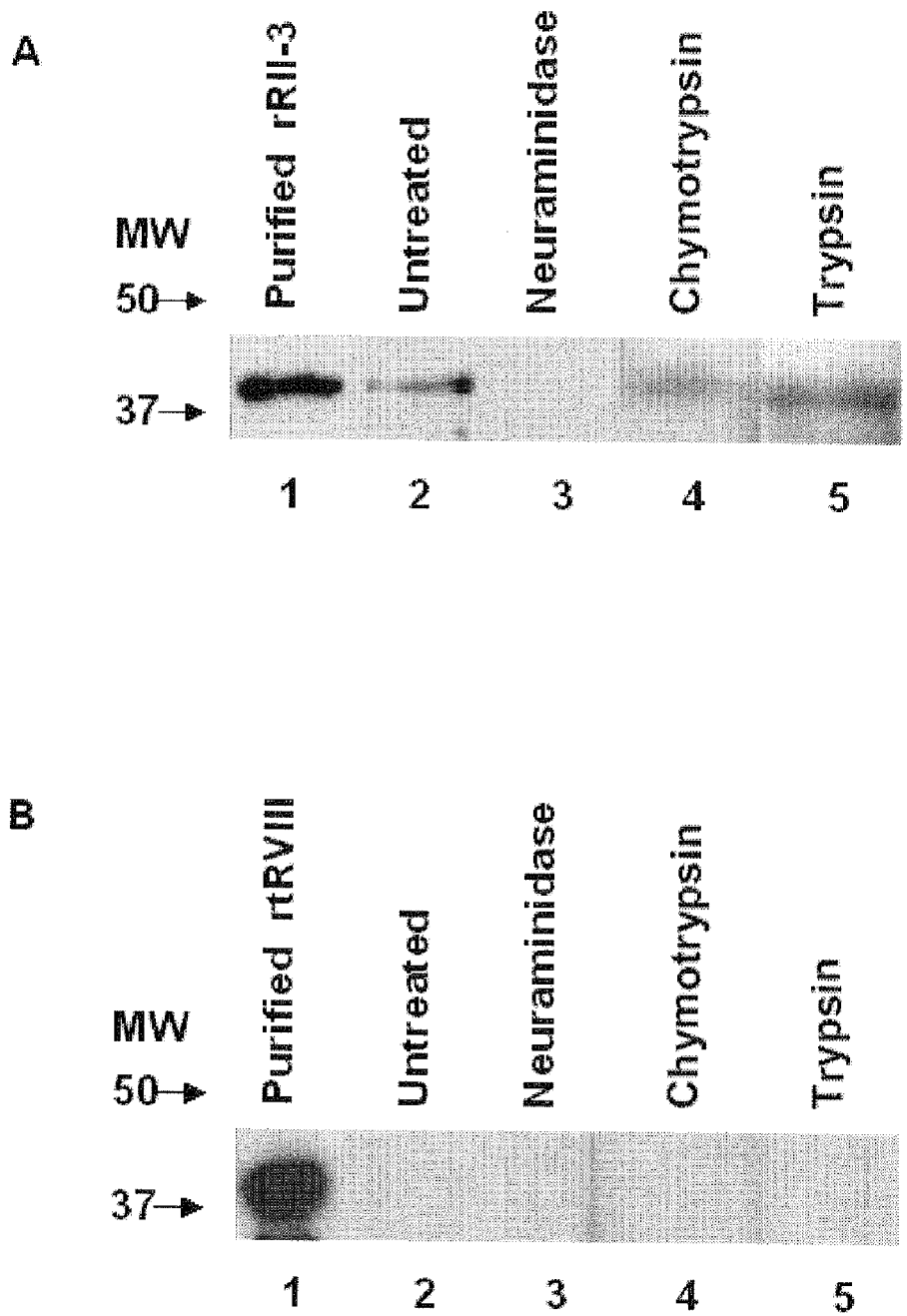
FIG. 4 represents erythrocyte-binding with recombinant protein rRII-3 or rtRVIII. Protein bound to erythrocytes was detected by Western blotting with anti-His mouse antibody. Erythrocyte-binding assay with purified rRII-3(A) or rtRVIII (B) Protein only (Lane 1), Protein bound to untreated erythrocytes (lane 2), Neuraminidase treated (lane 3), chymotrypsin treated (lane 4) and trypsin treated (lane 5) erythrocytes.

The DNA sequence of RII-3 (SEQ ID NO: 7) was amplified by PCR using primers SEQ ID NO: 33 and 34. The DNA sequence of tRVIII (SEQ ID NO:37) was amplified by PCR using primers SEQ ID NO: 35 and 36 to generate recombinant constructs in pET24a(+). The PCR products were digested with EcoRI and XhoI and cloned into *E. coli* expression vector pET24a(+) (Novagen) to generate a C-terminal His tag. *E. coli* strain, BL21-CodonPlus-RIL (kindly supplied by Prof. Julien Lescar, Nanyang Technological University, Singapore), was transformed with pET24a(+) constructs and used for expression of recombinant rRII-3 and rtRVIII. Luria Bertani (LB) containing kanamycin (Invitrogen) (50 ug/ml) and chloramphenicol (Invitrogen) (50 ug/ml) was inoculated with *E. coli* BL21-codonPlus-RIL transformed with pET24a(+) constructs and cultured overnight at 37° C. Fresh LB containing kanamycin (50 ug/ml) and chloramphenicol (50 ug/ml) was inoculated with the overnight culture at a dilution of 1:50 and cultured at 37° C. to an $A_{600\,nm}$ of 0.6-0.8. Expression of rRII-3 and rtRVII proteins was induced by adding isopropyl-1-thio-b-galactopyranoside (IPTG) (USB) to the culture at a final concentration of 0.2 mM. Induced cultures were allowed to grow overnight at 16° C. After induction, *E. coli* cells were harvested by centrifugation, resuspended in chilled lysis buffer (50 mM Tris, pH 8.0, 200 mM NaCl, 0.1% tween-20 with protease inhibitor cocktail, EDTA-free (Roche Applied Science) for rRII-3; 50 mM Tris, pH 8.5, 200 mM NaCl, with protease inhibitor cocktail, EDTA-free for rtRVIII), and lysed by sonication. The supernatant was collected by centrifugation of lysed cells at 4° C. Recombinant protein was purified under native conditions using nickel-nitrilotriacetic acid-agarose (Ni-NTA) as described by the manufacturer (Qiagen). The recombinant proteins were further purified by ion-exchange chromatography using a MonoS™ HR 5/5 column (Amersham Biosciences) for rRII-3 and MonoQ™ 5/50 GL column (Amersham Biosciences) for rtRVIII, following the manufacturer's protocol.
Erythrocyte-Binding Assay Using rRII-3 and rtRVIII Recombinant Proteins The recombinant protein named rRII-3 expressed in a soluble form with the expected molecular weight of approximately 40 kDa protein (FIG. 4A, lane 1) was also tested for its ability to bind erythrocytes. At the same time a construct expressing a similarly sized soluble protein of region VIII named rtRVIII was prepared as negative control (FIG. 4B, lane 1). Only, rRII-3 directly bound to erythrocytes (FIG. 4A) with no binding being detected for tRVIII in any of the conditions tested (FIG. 4B). Importantly, chymotrypsin- and trypsin-treated erythrocytes, but not in neuraminidase-treated erythrocytes are bound by rRII-3 (FIG. 4A). These results independently confirm that RII-3 is the erythrocyte binding region of PfRH1.
Amino-Acid Sequence Analysis and Identification of a New Erythrocyte Binding Domain in *Plasmodium*

Amino-acid sequence alignments were carried out using program BLAST (Altschul et al, 1997) and ClustalW (Thompson et al, 1994). The coiled-coils prediction was carried out using program COILS available on the world wide web at russell.embl.de/cgi-bin/coils-svr.pl. Secondary structure predictions were carried out according to the method of reference (Rost et al, 2003).

Inspection of the sequence of the 334 amino-acid long minimal binding fragment RII-3 (FIG. 5A) reveals a very uneven distribution of residues with Ala, Gly, Met, Cys, Pro, Trp absent or with respective occurrences <1% and a large excess of Ile (16.2%), Lys (14.7%), Gln (12.3%) and Leu (10.2%) residues. The presence of a heptad repeat motif with an Ile side chain at position "a" could be detected between residues 261 to 289. As a confirmation, the program COILS (Baum J, 2003) was used and indeed unambiguously detected a coiled coil region in the C-terminal domain of RII-3, centred at residue 275 (FIG. 5C). In the absence of a 3D structure, the exact length of this α-helical coiled coil is difficult to assess but is likely to span between 28 to 49 residues which translates into a helix of a length comprised between 43 to 75 Å. A weak sequence identity of 27% for 105 aligned amino-acids with the second Heptad repeat region B "HRB" of the parainfluenza virus F protein may be detected between amino-acids 201 to 304 of RII-3. Interestingly the corresponding HRB region spanning residues 378-479 of the parainfluenza F protein, participates in the formation of trimeric coiled coil of α-helices (Yin et al, 2006). Overall the RII-3 protein is predicted to be predominantly α-helical with a possible second coiled coil region centered at residue 125 (FIG. 5C). Between these two helical segments lies a region of approximately 70 residues spanning amino-acids 180 till 250 which is predicted to be richer in loop structures (FIG. 5C).

Having identified the binding region for PfRH1 it was important to determine whether this domain has conserved features seen in other members of the RH. Alignment and secondary structure prediction of the corresponding regions of other members of *P. falciparum* were performed using ClustalW sequence alignment program on the world wide web at .ebi.ac.uk/clustalw (Thompson et al, 1994). PfRH2a/b and PfRH4 indicate both amino acid and secondary structure conservation with approx. 65% similarity (FIG. 5A). As noted, PfRH3 is not shown in the alignment as it introduced too many gaps in the resulting alignment; on the other hand pair-alignment of PfRH1-RII-3 and PfRH3 indicates 56% similarity between these 2 regions. This conservation while clearly less pronounced is somewhat analogous to the DBL domains. The conserved region of PfRH1-RII-3 also can be found in other members of RH of different *Plasmodium* species (FIG. 5B) with more than 50% similarity. While overall sequence identity for all the regions is low they all are predicted to contain a coiled coil region in the C-terminal domain consistent with an overall structural conservation of the domain. Predicted binding regions of RH orthologues in *P. falciparum* and *P. vivax* are shown in FIG. 6. The binding regions were identified using the PfRHi-RII-3 vs predicted binding regions of other RH members (ClustalW).
Generation of Antibodies Against Recombinant Proteins rRII-3 and rtRVIII Purified recombinant proteins, rRII-3 and rtRVIII were used to immunize mice to raise the antisera αrRII-3 and αrtRVIII. In order to determine whether the antisera are able to recognize PfRH1 protein, we performed Western blotting of *P. falciparum* W2mef merozoite extracts probed with αrRII-3 and αrtRVIII respectively. Mouse pre immune serum and normal RBC lysate were also used to test the antisera specificity. Previous work had shown that an approximately 240 kDa protein is recognized by PfRH1 specific sera in W2mef (Baum et al., 2003) and a similarly sized protein was detected with both antisera αrRII-3 and αrtRVIII raised (FIG. 7A). No protein was detected by mouse pre-immune serum or in normal RBC lysate using αrRII-3 or αrtRVIII. In Immunofluorescence Assays (IFAs) using fixed parasites both rRII-3 and rtRVIII antisera gave a punctuate pattern in schizonts consistent with the expression at the apical end of merozoites (FIGS. 7 B and C). No staining was observed in mouse preimmune serum (FIG. 7 D). These results show that the two antisera are specific for PfRH1 protein.
Invasion Inhibition Assay of *P. falciparum* W2mef in the Presence of αrRII-3 and αrtRVIII.

We then investigated whether the different dilutions of the sera raised exhibited different effects on invasion of the parasites (FIG. 7E). Invasion inhibition assays performed on synchronized cultures showed the ability of the αrRII-3 and αrtRVIII antisera to inhibit invasion. The pre-immune serum had no significant effect on invasion in all the parasites studied. On the other hand antiserum αrRII-3, raised against the minimal binding region of PfRH1, successfully blocked invasion in W2mef up to 70% at a 1:10 dilution. Furthermore, the αrRVIII showed minimal or no inhibition for at all dilutions of the antibody. The invasion inhibition assay demonstrates that antiserum raised against the binding domain of PfRH1 (RII-3) contains more efficient invasion inhibitory antibodies then those raised against another region of the protein.

REFERENCES

1. Altschul S F, Madden T L, Schaffer A A, et al. Gapped BLAST and PSI-BLAST: a new generation of protein database search programs. Nucleic Acids Res. 1997; 25:3389-3402.
2. Baum J, Pinder M, Conway D J. Erythrocyte invasion phenotypes of *Plasmodium falciparum* in The Gambia. Infect Immun. 2003; 71:1856-1863.

3. Chitnis C E, Miller L H. Identification of the erythrocyte binding domains of *Plasmodium vivax* and *Plasmodium knowlesi* proteins involved in erythrocyte invasion. J Exp Med. 1994; 180:497-506.
4. Cowman A F, Crabb B S. Invasion of red blood cells by malaria parasites. Cell. 2006; 124:755-766.
5. Duraisingh, M. T., Triglia, T., Ralph, S. A., Rayner, J. C., Barnwell, J. W., McFadden, G. I., and Cowman, A. F. (2003b). Phenotypic variation of *Plasmodium falciparum* merozoite proteins directs receptor targeting for invasion of human erythrocytes. Embo J 22, 1047-1057.
6. Gaur, D., Mayer, D. C., and Miller, L. H. (2004) Parasite ligand-host receptor interactions during invasion of erythrocytes by *Plasmodium* merozoites. Int J Parasitol 34: 1413-1429.
7. Jayasree Iyer, Anne Charlotte Grüner, Laurent Rénia, Georges Snounou and Peter R. Preiser. Invasion of host cells by malaria parasites: A tale of two protein families. 2007 Mol. Microbiol. 65(2):231-249
8. Mayer D C, Mu J B, Kaneko O, Duan J, Su X Z, Miller L H. Polymorphism in the *Plasmodium falciparum* erythrocyte-binding ligand JESEBL/EBA-181 alters its receptor specificity. Proc Natl Acad Sci USA. 2004; 101:2518-2523.
9. Michon, P., Fraser, T., and Adams, J. H. (2000). Naturally acquired and vaccine-elicited antibodies block erythrocyte cytoadherence of the *Plasmodium vivax* Duffy binding protein. Infect Immun 68, 3164-3171.
10. Rayner J C, Vargas-Serrato E, Huber C S, Galinski M R, Barnwell J W. A *Plasmodium falciparum* homologue of *Plasmodium vivax* reticulocyte binding protein (PvRBP1) defines a trypsin-resistant erythrocyte invasion pathway. J Exp Med. 2001; 194:1571-1581.
11. Rost B, Liu J. The PredictProtein server. Nucleic Acids Res. 2003; 31:3300-3304.
12. Sim B K L, Chitnis C E, Wasniowska K, Hadley T J, Miller L H. Receptor and ligand domains for invasion of erythrocytes by *Plasmodium falciparum*. Science. 1994; 264:1941-1944.
13. Snow R W, Guerra C A, Noor A M, Myint H Y, Hay S I. The global distribution of clinical episodes of *Plasmodium falciparum* malaria. Nature. 2005; 434:214-217.
14. Thompson J D, Higgins D G, Gibson T J. CLUSTAL W: improving the sensitivity of progressive multiple sequence alignment through sequence weighting, position-specific gap penalties and weight matrix choice. Nucleic Acids Res. 1994; 22:4673-4680.
15. Yin H S, Wen X, Paterson R G, Lamb R A, Jardetzky T S. Structure of the parainfluenza virus 5 F protein in its metastable, prefusion conformation. Nature. 2006; 439:38-44.

The invention claimed is:

1. An isolated polypeptide, wherein the polypeptide is a *Plasmodium* RH fragment, comprising SEQ ID NO: 8, wherein the polypeptide is less than 700 amino acids.

2. The isolated polypeptide of claim 1, wherein the polypeptide sequence is selected from the fragments of *Plasmodium falciparum* reticulocyte homologue 1 (PfRH1), and *Plasmodium vivax* reticulocyte Binding Protein homologue (PvRBP1).

3. A pharmaceutical composition for reducing or inhibiting the binding to or invasion of *Plasmodium* into erythrocytes, comprising the polypeptide of claim 1 and optionally in the presence of at least one pharmaceutically acceptable excipient, diluent, carrier and/or a combination thereof.

4. A method of treating or inhibiting development of malaria comprising administering to a subject in need a composition comprising the polypeptide of claim 1.

5. The method according to claim 4, wherein the method comprises reducing or inhibiting the binding to or invasion of *Plasmodium* into erythrocytes.

6. A method of inducing a protective immune response to at least one *Plasmodium* merozoite in a subject comprising administering to the subject an immunologically effective amount of at least one polypeptide of claim 1, optionally in combination with pharmaceutically acceptable excipient, carrier, additive, adjuvant or combination thereof.

* * * * *